(12) United States Patent
Beckett et al.

(10) Patent No.: US 6,503,897 B1
(45) Date of Patent: *Jan. 7, 2003

(54) ANTIBACTERIAL AGENTS

(75) Inventors: Raymond Paul Beckett, Oxford (GB); Mark Whittaker, Oxford (GB); Zoe Marie Spavold, Oxford (GB)

(73) Assignee: British Biotech Pharmaceuticals Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/914,049

(22) PCT Filed: Mar. 28, 2000

(86) PCT No.: PCT/GB00/01175

§ 371 (c)(1), (2), (4) Date: Aug. 22, 2001

(87) PCT Pub. No.: WO00/58294

PCT Pub. Date: Oct. 5, 2000

(30) Foreign Application Priority Data

Mar. 29, 1999 (GB) ................................................ 9907055

(51) Int. Cl.$^7$ .................. C07D 281/06; C07D 267/10; C07D 245/02; A61K 31/554; A61K 31/553

(52) U.S. Cl. ............ 514/183; 514/211.03; 514/211.07; 514/212.03; 514/218; 514/327; 514/431; 540/460; 540/463; 540/488; 540/491; 540/492; 540/527; 546/221; 549/10

(58) Field of Search .................................. 540/460, 463, 540/488, 491, 492, 527; 546/221; 549/10; 514/183, 211.03, 211.07, 212.03, 218, 327, 431

(56) References Cited

FOREIGN PATENT DOCUMENTS

| WO | 95/04735 | 2/1995 |
|---|---|---|
| WO | 96/23791 | 8/1996 |
| WO | 97/38705 | 10/1997 |
| WO | 99/39704 | 8/1999 |
| WO | 99/61413 | 12/1999 |

OTHER PUBLICATIONS

Haag et al., Derwent Abstract for DE 3,320,175, 1984.*

* cited by examiner

*Primary Examiner*—Deepak R. Rao
(74) *Attorney, Agent, or Firm*—Banner & Witcoff, Ltd.

(57) ABSTRACT

Compounds of formula (I) are antibacterial agents wherein: $R_3$ and $R_4$, taken together with the carbon atoms to which they are respectively attached, form an optionally substituted saturated carbocyclic or heterocyclic ring of 5 to 16 atoms, which may be benz-fused or fused to a second optionally substituted saturated carbocyclic or heterocyclic ring of 5 to 16 atoms; and $R_1$ and $R_2$ are as defined in the specification.

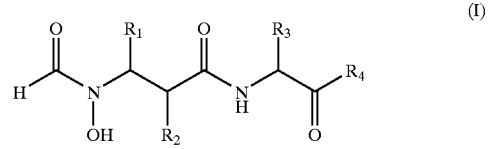

9 Claims, No Drawings

ANTIBACTERIAL AGENTS

This invention relates to a novel class of N-formyl hydroxylamine derivatives having antibacterial activity, and to pharmaceutical and veterinary compositions comprising such compounds.

BACKGROUND OF THE INVENTION

In general, bacterial pathogens are classified as either Gram-positive or Gram-negative. Many antibacterial agents (including antibiotics) are specific against one or other Gram-class of pathogens. Antibacterial agents effective against both Gram-positive and Gram-negative pathogens are therefore generally regarded as having broad-spectrum activity.

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those which have mechanisms of action fundamentally different from the known classes.

Amongst the Gram-positive pathogens, such as Staphylococci, Streptococci, Mycobacteria and Enterococci, resistant strains have evolved/arisen which makes them particularly difficult to eradicate. Examples of such strains are methicillin resistant *Staphylococcus aureus* (MRSA), methicillin resistant coagulase negative Staphylococci (MRCNS), penicillin resistant *Streptococcus pneumoniae* and multiply resistant *Enterococcus faecium*.

Pathogenic bacteria are often resistant to the aminoglycoside, β-lactam (penicillins and cephalosporins), and chloramphenicol types of antibiotic. This resistance involves the enzymatic inactivation of the antibiotic by hydrolysis or by formation of inactive derivatives. The β-lactam (penicillin and cephalosporin) family of antibiotics are characterised by the presence of a β-lactam ring structure. Resistance to this family of antibiotics in clinical isolates is most commonly due to the production of a "penicillinase" (β-lactamase) enzyme by the resistant bacterium which hydrolyses the β-lactam ring thus eliminating its antibacterial activity.

Recently there has been an emergence of vancomycin-resistant strains of enterococci (Woodford N. 1998 Glycopeptide-resistant enterococci: a decade of experience. Journal of Medical Microbiology. 47(10):849–62). Vancomycin-resistant enterococci are particularly hazardous in that they are frequent causes of hospital based infections and are inherently resistant to most antibiotics. Vancomycin works by binding to the terminal D-Ala-D-Ala residues of the cell wall peptidioglycan precursor. The high-level resistance to vancomycin is known as VanA and is conferred by a genes located on a transposable element which alter the terminal residues to D-Ala-D-lac thus reducing the affinity for vancomycin.

In view of the rapid emergence of multidrug-resistant bacteria, the development of antibacterial agents with novel modes of action that are effective against the growing number of resistant bacteria, particularly the vancomycin resistant enterococci and β-lactam antibiotic-resistant bacteria, such as methicillin-resistant *Staphylococcus aureus*, is of utmost importance.

BRIEF DESCRIPTION OF THE INVENTION

This invention is based on the finding that certain N-formyl hydroxylamine derivatives have antibacterial activity, and makes available a new class of antibacterial agents.

Although it may be of interest to establish the mechanism of action of the compounds with which the invention is concerned, it is their ability to inhibit bacterial growth, which makes them useful. However, it is presently believed that their antibacterial activity is due, at least in part, to intracellular inhibition of bacterial polypeptide deformylase (PDF) enzyme.

Bacterial polypeptide deformylases (PDF) (EC 3.5.1.31), are a conserved family of metalloenzymes (Reviewed: Meinnel T, Lazennec C, Villoing S, Blanquet S, 1997, Journal of Molecular Biology 267, 749–761) which are essential for bacterial viability, their function being to remove the formyl group from the N-terminal methionine residue of ribosome-synthesised proteins in eubacteria. Mazel et al. (EMBO J. 13(4):914–923, 1994) have recently cloned and characterised an *E. coli* PDF. As PDF is essential to the growth of bacteria and there is no eukaryotic counterpart to PDF, Mazel et al. (ibid), Rajagopalan et al. (J. Am. Chem. Soc. 119:12418–12419, 1997) and Beckeretal., (J. Biol Chem. 273(19):11413–11416, 1998) have each proposed that PDF is an excellent anti-bacterial target.

Certain N-formyl hydroxylamine derivatives have previously been claimed in the patent publications listed below, although very few examples of such compounds have been specifically made and described:

EP-B-0236872 (Roche)
WO 92/09563 (Glycomed)
WO 92/04735 (Syntex)
WO 95/19965 (Glycomed)
WO 95/22966 (Sanofi Winthrop)
WO 95/33709 (Roche)
WO 96/23791 (Syntex)
WO 96/16027 (Syntex/Agouron)
WO 97/03783 (British Biotech)
WO 97/18207 (DuPont Merck)
WO 98/38179 (GlaxoWelicome)
WO 98/47863 (Labs Jaques Logeais)

The pharmaceutical utility ascribed to the N-formyl hydroxylamine derivatives in those publications is the ability to inhibit matrix metalloproteinases (MMPs) and in some cases release of tumour necrosis factor (TNF), and hence the treatment of diseases or conditions mediated by those enzymes, such as cancer and rheumatoid arthritis. That prior art does not disclose or imply that N-formyl hydroxylamine derivatives have antibacterial activity.

In addition to these, U.S. Pat. No. 4,738,803 (Roques et al.) also discloses N-formyl hydroxylamine derivatives, however, these compounds are disclosed as enkephalinase inhibitors and are proposed for use as antidepressants and hypotensive agents. Also, WO 97/38705 (Bristol-Myers Squibb) discloses certain N-formyl hydroxylamine derivatives as enkephalinase and angiotensin converting enzyme inhibitors. This prior art does not disclose or imply that N-formyl hydroxylamine derivatives have antibacterial activity either.

Our copending International patent application no. PCT/GB99/00386 discloses that certain N-formyl hydroxylamine derivatives have antibacterial activity. One class of compounds disclosed as having such activity has general formula (IA):

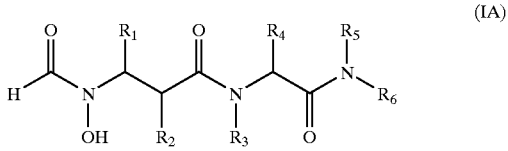

(IA)

wherein the various "R" substituents are as specified in the document. The compounds useful in accordance with the present invention differ in structure from those of PCT/GB99/00386 principally in that the acyclic amidoalkyl radical shown as lying to the right of the curved line in formula (IA) is replaced by a cyclic radical.

DETAILED DESCRIPTION IF THE INVENTION

According to the first aspect of the present invention there is provided a compound of formula (I) or a pharmaceutically or veterinarily acceptable salt, hydrate or solvate thereof:

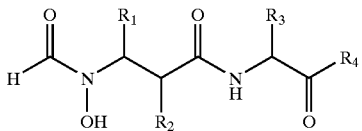

(I)

wherein:
$R_1$ represents hydrogen, methyl, or trifluoromethyl
$R_2$ represents a group $R_{10}\text{-}(X)_n\text{-}(ALK)\text{-}$ wherein
  Rl, represents hydrogen, a $C_1\text{-}C_6$ alkyl, $C_2\text{-}C$ alkenyl, $C_2\text{-}C_6$ alkynyl, cycloalkyl, aryl, or heterocyclyl group, any of which may be unsubstituted or substituted by $(C_1\text{-}C_6)$alkyl, $(C_1\text{-}C_6)$alkoxy, hydroxy, mercapto, $(C_1\text{-}C_6)$alkylthio, amino, halo (including fluoro, chloro, bromo and iodo), trifluoromethyl, cyano, nitro, -COOH, $-CONH_2$, $-COOR^A$, $-NHCOR^A$, $-CONHR^A$, $-NHR^A$, $-NR^AR$, or $-CONR^AR^B$ wherein $R^A$ and $R^B$ are independently a $(C_1\text{-}C_6)$alkyl group, and
  ALK represents a straight or branched divalent $C_1\text{-}C_6$ alkylene, $C_2\text{-}C_6$ alkenylene, $C_2\text{-}C_6$ alkynylene radical, and may be interrupted by one or more non-adjacent —NH—, —O— or —S— linkages,
  X represents —NH—, —O— or —S—, and
  n is 0 or 1; and
$R_3$ and $R_4$, taken together with the carbon atoms to which they are respectively attached, form an optionally substituted saturated carbocyclic or heterocyclic ring of 5 to 16 atoms, which may be benz-fused or fused to a second optionally substituted saturated carbocyclic or heterocyclic ring of 5 to 16 atoms.

In another aspect, the invention provides the use of a compound of formula (I) as defined above in the preparation of a composition for treatment of bacterial infections in humans and non-human mammals.

In another aspect, the invention provides a method for the treatment of bacterial infections in humans and non-human mammals, which comprises administering to a subject suffering such infection an antibacterially effective dose of a compound of formula (I) as defined above.

In a further aspect of the invention there is provided a method for the treatment of bacterial contamination by applying an antibacterially effective amount of a compound of formula (I) as defined above to the site of contamination.

The compounds of formula (I) as defined above may be used as component(s) of antibacterial cleaning or disinfecting materials.

On the hypothesis that the compounds (I) act by inhibition of intracellular PDF, the most potent antibacterial effect may be achieved by using compounds which efficiently pass through the bacterial cell wall. Thus, compounds which are highly active as inhibitors of PDF in vitro and which penetrate bacterial cells are preferred for use in accordance with the invention. It is to be expected that the antibacterial potency of compounds which are potent inhibitors of the PDF enzyme in vitro, but are poorly cell penetrant, may be improved by their use in the form of a prodrug, ie a structurally modified analogue which is converted to the parent molecule of formula (I), for example by enzymic action, after it has passed through the bacterial cell wall.

As used herein the term "$(C_1\text{-}C_6)$alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

As used herein the term "divalent $(C_1\text{-}C_6)$alkylene radical" means a saturated hydrocarbon chain having from 1 to 6 carbon atoms and two unsatisfied valencies.

As used herein the term "$(C_2\text{-}C_6)$alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl.

As used herein the term "divalent $(C_2\text{-}C_6)$alkenylene radical" means a hydrocarbon chain having from 2 to 6 carbon atoms, at least one double bond, and two unsatisfied valencies.

As used herein the term "$C_2\text{-}C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent $(C_2\text{-}C_6)$alkynylene radical" means a hydrocarbon chain having from 2 to 6 carbon atoms, at least one triple bond, and two unsatisfied valencies.

As used herein the term "cycloalkyl" means a saturated alicyclic moiety having from 3–8 carbon atoms and includes, for example, cyclopropyl, cyclobutyl, cyclopentyl, cyclohexyl, cycloheptyl and cyclooctyl.

As used herein the term "cycloalkenyl" means an unsaturated alicyclic moiety having from 3–8 carbon atoms and includes, for example, cyclopropenyl, cyclobutenyl, cyclopentenyl, cyclohexenyl, cycloheptenyl and cyclooctenyl. In the case of cycloalkenyl rings of from 5–8 carbon atoms, the ring may contain more than one double bond.

As used herein the term "aryl" refers to a mono-, bi- or tri-cyclic carbocyclic aromatic group, and to groups consisting of two covalently linked monocyclic carbocyclic aromatic groups. Illustrative of such groups are phenyl, biphenyl and napthyl.

As used herein the term "heteroaryl" refers to a 5- or 6-membered aromatic ring containing one or more heteroatoms, and optionally fused to a benzyl or pyridyl ring; and to groups consisting of two covalently linked 5- or 6-membered aromatic rings each containing one or more heteroatoms; and to groups consisting of a monocyclic carbocyclic aromatic group covalently linked to a 5- or 6-membered aromatic rings containing one or more heteroatoms. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, 4-([1,2,3]-thiadiazoly4-yl)phenyl and 5-isoxazol-3-ylthienyl.

As used herein the unqualified term "carbocyclyl" or "carbocyclic" refers to a 5–8 membered ring whose ring atoms are all carbon.

As used herein the unqualified term "heterocyclyl" or "heterocyclic" includes "heteroaryl" as defined above, and in particular means a 5–8 membered aromatic or non-aromatic heterocyclic ring containing one or more heteroatoms selected from S, N and O, and optionally fused to a benzene ring, including for example, pyrrolyl, furyl, thienyl, piperidinyl, imidazolyl, oxazolyl, thiazolyl, thiadiazolyl, thiazepinyl, pyrazolyl, pyridinyl, pyrrolidinyl, pyrimidinyl, morpholinyl, piperazinyl, indolyl, benzimidazolyl, maleimido, succinimido, phthalimido and 1,3-dioxo-1,3-dihydro-isoindol-2-yl groups.

Unless otherwise specified in the context in which it occurs, the term "substituted" as applied to any moiety herein means substituted with up to four substituents, each of which independently may be ($C_1$–$C_6$)alkyl, benzyl, ($C_1$–$C_6$)alkoxy, phenoxy, hydroxy, mercapto, ($C_1$–$C_6$) alkylthio, amino, halo (including fluoro, chloro, bromo and iodo), trifluoromethyl, nitro, -COOH, -CONH$_2$, -COR$^A$, -COOR$^A$, -NHCOR$^A$, -CONHR$^A$, -NHR$^A$, -NR$^A$R$^B$, or -CONR$^A$R$^B$ wherein R$^A$ and R$^B$ are independently a ($C_1$–$C_6$) alkyl group. In the case where "substituted" means benzyl, the phenyl ring thereof may itself be substituted with any of the foregoing, except benzyl.

There are at least two actual or potential chiral centres in the compounds according to the invention because of the presence of asymmetric carbon atoms. The presence of several asymmetric carbon atoms gives rise to a number of diastereoisomers with R or S stereochemistry at each chiral centre. The invention includes all such diastereoisomers and mixtures thereof. Currently, the preferred stereoconfiguration of the carbon atom carrying the $R_2$ group is R; and that of the carbon atom carrying the $R_1$ group (when asymmetric) is R.

In the compounds of formula (1) as defined above:

$R_1$ may be, for example, hydrogen, methyl, or trifuoromethyl. Hydrogen is currently preferred.

$R_2$ may be, for example:

optionally substituted $C_1$–$C_8$ alkyl, $C_3$–$C_6$ alkenyl, $C_3$–$C_6$ alkynyl or cycloalkyl;

phenyl($C_1$–$C_6$ alkyld, phenyl($C_3$–$C_6$ alkenyl)- or phenyl ($C_3$–$C_6$ alkynyl)- optionally substituted in the phenyl ring;

cycloalkyl($C_1$–$C_6$ alkyl)-, cycloalkyl($C_3$–$C_6$ alkenyl)- or cycloalkyl($C_3$–$C_6$ alkynyl)- optionally substituted in the cycloalkyl ring;

heterocyclyl($C_1$–$C_6$ alkyl)-, heterocyclyl ($C_3$–$C_6$ alkenyl)- or heterocyclyl($C_3$–$C_6$ alkynyl)- optionally substituted in the heterocyclyl ring; or $CH_3(CH_2)_pO(CH_2)_q$- or $CH_3(CH_2)_pS(CH_2)_q$-, wherein p is 0, 1, 2 or 3 and q is 1, 2or 3.

Thus, $R_2$ may be, for example, $C_1$–$C_6$ alkyl, $C_3$–$C_6$ alkenyl or $C_3$–$C_6$ alkynyl;

phenyl($C_1$–$C_6$ alkyl)-, phenyl($C_3$–$C_6$ alkenyl)- or phenyl ($C_3$–$C_6$ alkynyl)-optionally substituted in the phenyl ring;

cycloalkyl($C_1$–$C_6$ alkyl)-, cycloalkyl($C_3$–$C_6$ alkenyl)- or cycloalkyl($C_3$–$C_6$ alkynyl)- optionally substituted in the phenyl ring;

heterocyclyl($C_1$–C, alkyl)-, heterocyclyl($C_3$–$C_6$ alkenyl)- or heterocyclyl($C_3$–$C_6$ alkynyl)- optionally substituted in the heterocyclyl ring; or 4-phenylphenyl($C_1$–$C_6$ alkyl)-, 4-phenylphenyl($C_3$–$C_6$ alkenyl)-, 4-phenylphenyl($C_3$–$C_6$ alkynyl)-, 4-heteroarylphenyl($C_1$–$C_6$ alkyl)-, 4-heteroarylphenyl ($C_3$–$C_6$ alkenyl)-, 4-heteroarylphenyl($C_3$–$C_6$ alkynyl)-, optionally substituted in the terminal phenyl or heteroaryl ring.

Specific examples of $R_2$ groups include methyl, ethyl, n- and iso-propyl, n- and iso-butyl, n-pentyl, iso-pentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, or 4-methoxybenzyl.

Presently preferred groups at $R_2$ are n-propyl, n-butyl, n-pentyl, benzyl and cyclopentylmethyl.

$R_3$ and $R_4$, taken together with the carbon atoms to which they are respectively attached, form an optionally substituted monocyclic saturated carbocyclic or heterocyclic ring of 5 to 16 atoms, for example from 5 to 8 atoms. Referring to formula (I), the carbon atom shown as carrying the group $R_3$ is the one linking the ring to the rest of the molecule, and may arbitrarily be numbered as the 1- position in the ring. The carbon atom shown as carrying the $R_4$ group is adjacent the 1-position, and is oxo- (keto-) substituted. The remaining atoms in the ring may all be carbons, or may include one or more hetero atoms —O—, —S— or —N($R_5$)— wherein $R_5$ may be hydrogen, a $C_1$–$C_4$alkyl group, a phenyl or benzyl group, or an acyl radical (for example phenylcarbonyl) or sulphonyl radical (for example 4-methoxyphenylsulphonyl or 4-trifluoromethylphenylsulphonyl).

More than one hetero-atom may be present in the ring, but it will be appreciated that unstable combinations such as adjacent —O— atoms will not be feasible. Where the ring contains an S atom, it may be oxidised as a sulphinyl or sulphonyl. In one particular embodiment, the ring atom in the 3-position is —N($R_5$)— wherein $R_5$ may be hydrogen or a $C_1$–$C_4$alkyl, phenyl or benzyl group. In another embodiment the ring contains one —O— or —S— atom. In still another embodiment the ring contains one —O— or —S— atom and a nitrogen atom separated by carbon atom(s). In yet another embodiment, the ring contains two or three nitrogen atoms.

In general, the radical formed by $R_3$ and $R_4$, taken together with the carbon atoms to which they are respectively attached may be represented schematically as formula (II)

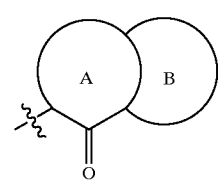

(II)

wherein rings A and B each have 5–8 ring atoms which may include heteroatoms and which may each be substituted. Ring B is optional, and may be a fused benzene ring or a second 5–8 membered saturated carbocyclic or heterocyclic ring.

The ring formed by $R_3$ and $R_4$, taken together with the carbon atoms to which they are respectively attached, may be substituted (as defined above). In one particular embodiment the ring atom in position n of an n-membered ring (n being 5, 6, 7 or 8 and numbering from position 1, with the oxo-substituted carbon atom being position 2) may be a carbon atom substituted by one or two methyl groups, and the ring atom in position n-1 may be a sulphur atom. Examples of such rings, formed by $R_3$ and $R_4$, taken together with the carbon atoms to which they are respectively attached, are those of the following structure (III):

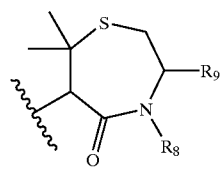

(III)

wherein $R_8$ may be hydrogen or a $C_1$–$C_4$alkyl (eg methyl, ethyl or n-propyl), cycloalkyl (eg cyclopentyl) phenyl or benzyl group, and R, may be hydrogen or a $C_1$–$C_4$alkyl (eg isobutyl), phenyl or benzyl group, or $R_8$ and $R_9$ taken together represent a divalent —$(CH_2)_p$— radical wherein p is 3 or 4.

Specific examples of radicals having the general structure (II) include 4,7,7-trimethyl-5-oxo-[1,4]thiazepan-6-yl
3-benzyl4,7,7- trimethyl-5-oxo-[1,4]thiazepan-6-yl
3,3-dimethyl-5-oxo- hexahydro-pyrrolo[2,1-c][1,4]thiazepin4-yl
7,7-dimethyl-5-oxo- octahydro-8-thia-4a-aza-benzocyclohepten-6-yl
7,7-dimethyl-5-oxo-octahydro-8-thia4a-aza-benzocycloocten-6-yl
4-ethyl-7,7-dimethyl-5- oxo-[1,4]thiazepan-6-yl
7,7-dimethyl-5-oxo4-propyl-[1,4]thiazepan-6-yl
7,7-dimethyl-5-oxo4-phenyl-[1,4]thiazepan-6-yl
7,7-dimethyl-5-oxo-4- phenyl-[1,4]thiazepan-6-yl
1-methyl-2-oxo-azepan-3-yl
1-benzyl-2-oxo-piperidin-3-yl
1-methyl-2,5-dioxo-pyrrolidin-3-yl
4-methyl-3,5-dioxo-[1,4]oxazepan-6-yl
4-methyl-3,5-dioxo-[1,4]thiazepan-6-yl
1-methyl-2,7-dioxo-azepan-3-yl
1-methyl-2,6-dioxo-piperidin-3-yl
1-methyl-2-oxo-1,2,3,4-tetrahydro-quinolin-3-yl
2-methyl-3-oxo-2,3,4,5-tetrahydro-1H-benzo[c]azepin4-yl
1-methyl-2-oxo-2,3,4,5-tetrahydro-1H-benzo[b]azepin-3-yl
9-methyl-8-oxo-6,7,8,9-tetrahydro-5-oxa-9-aza-benzocyclohepten-7-yl
1-methyl-7-oxo-[1,4]diazepan-6-yl
1-(4-methoxy-benzenesulfonyl)4-methyl-5-oxo-[1,4]diazepan-6-yl
1-benzoyl-4-methyl-5-oxo-[1,4]diazepan-6-yl
1,4-dimethyl-5-oxo-[1,4]diazepan-6-yl
3-benzyl-5-oxo-[1,4]thiazepan-6-yl
3-benzyl-4-methyl-1,1,5-trioxo-[1,4]thiazepan-6-yl
2-benzyl-7-oxo-[1,4]oxathiepan-6-yl and
4-oxo-thiepan-3-yl.

Specific examples of compounds of the invention include those specifically named and characterised in the Examples herein.

Compounds of the invention may be prepared by a process comprising coupling an acid of formula (IV) with an amine of formula (V)

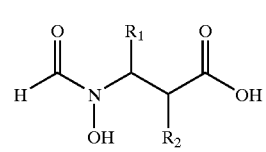

(IV)

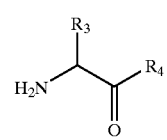

(V)

wherein $R_1$, $R_2$, $R_3$ and $R_4$ are as defined in relation to formula (I). The N-hydroxy group of compound (IV) is preferably protected during the coupling reaction, and the hydroxy group subsequently regenerated.

Compounds of formula (V) may be prepared by cyclisation of compounds of formula (VA)

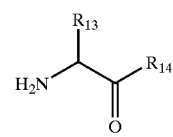

(VA)

wherein one of $R_{13}$ and $R_{14}$ contains a reactive group capable of reacting with a reactive partner site on the other of $R_{13}$ and $R_{14}$ to form a covalent bond between $R_{13}$ and $R_{14}$, thereby forming the desired ring, represented in formula (1) by $R_3$ and $R_4$ taken together with the carbon atoms to which they are respectively attached. During this cyclisation reaction, the amino group of (VA) will usually be protected, and the amino group subsequently released. Such intramolecular cyclisations, for example intramolecular condensation reactions, are known in the synthetic chemistry art. Alternatively, compounds of formula (V) may be prepared by reaction of a compound of formula (VB)

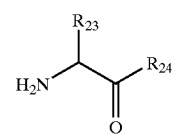

(VB)

with a bifunctional linker schematically represented as $X_1$—L—$X_2$, wherein $X_1$ is a reactive group capable of reacting with a reactive partner site in $R_{23}$, $X_2$ is a reactive group capable of reacting with a reactive partner site in $R_{24}$, and $R_{23}$, $R_{24}$ and L are chosen such that after reaction of $X_1$ and $X_2$ with their respective reactive partner sites, L forms a covalently linked bridge between $R_{23}$ and $R_{24}$ and completes the desired ring, represented in formula (I) by $R_3$ and $R_4$ taken together with the carbon atoms to which they are respectively attached. Again, during this cyclisation reaction, the amino group of (VA) will usually be protected, and the amino group subsequently released.

Again such intra molecular cyclisation by ring formation is known in the art of synthetic chemistry. Example 1 below is one illustration of such a reaction. Such reactions are preferably carried out at high dilution to maximise intramolecular rather than intermolecular bridge formation.

Compounds of the invention may also be accessible by cyclisation of a compound of formula (VI)

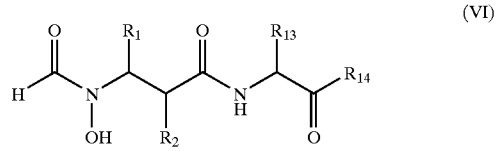

(VI)

wherein $R_1$ and $R_2$ are as defined in relation to formula (1), and $R_{13}$ and $R_{14}$ are as defined in relation to formula (VA). Preferably the N-formyl hydroxylamine group in (VI) is protected during the cyclisation reaction and the protecting group subsequently removed, or may be attached to a solid phase support (eg a resin), and subsequently released.

Alternatively, compounds of the invention may be accessible by reaction of a compound of formula (VIA)

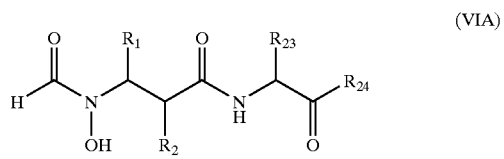

(VIA)

with a bifunctional linker schematically represented as $X_1$—L—$X_2$, wherein $R_1$ and $R_2$ are as defined in relation to formula (1), and $X_1$, $X_2$ and L are as defined in relation to formula (VB). Preferably the N-formyl hydroxylamine group in (V) is protected during the bridging reaction and the protecting group subsequently removed, or may be attached to a solid phase support (eg a resin), and subsequently released.

Antibacterial compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the active ingredient(s) may be made up into a cream, lotion or ointment. Cream or ointment formulations which may be used for the drug are conventional formulations well known in the art, for example as described in standard textbooks of pharmaceutics such as the British Pharmacopoeia.

The active ingredient(s) may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle. Intra-venous infusion is another route of administration for the compounds used in accordance with the invention.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The finding that compounds with PDF inhibitory activity can inhibit or prevent bacterial growth, opens up a novel approach for identifying new antibacterial agents by screening test compounds for activity as inhibitors of PDF in vitro, followed by confirmation of their antibacterial ability using bacterial growth inhibition studies. This finding also makes available (i) the use of compounds with PDF inhibitory activity as antibacterial agents, and (ii) a method for the treatment of bacterial infection or contamination by applying or administering a compound which inhibits the activity of bacterial PDF.

The following example illustrates an embodiment of the invention.

The following abbreviations have been used throughout:
DMF N,N-Dimethylformamide
EDC N-Ethyl-N'-(3-dimethylaminopropyl)carbodiimide hydrochloride
TFA Trifluoroacetic acid
HOAt 1-Hydroxy-7-aza-benzotriazole
HOBt 1-Hydroxybenzotriazole
HPLC High performance liquid chromatography
LRMS Low resolution mass spectrometry
TLC Thin layer chromatography
$^1$H and $^{13}$C NMR spectra were recorded using a Bruker AC 250E spectrometer at 250.1 and 62.9 MHz, respectively. Mass spectra were obtained using a Perkin Elmer Sciex API 165 spectrometer using both positive and negative ion modes.

The starting materials 2R-(tert-butoxyamino-methyl)-hexanoic acid and 2R-[(tert-butoxy-formyl-amino)-methyl]-hexanoic acid pentafluorophenyl ester were prepared as described below (see also Scheme 1). The starting materials 2R-[(benzyloxy amino)-methyl]-hexanoic acid and 2R-[(benzyloxy-formyl-amino)-methyl]-hexanoic acid pentafluorophenyl ester were prepared in a similar fashion.
STEP 1: 2-Butyl-acrylic Acid Butylmalonic acid (25 g, 156 mmol) was dissolved in ethanol (250 ml) and 37% formaldehyde solution (15.45 ml, 156 mmol) was added followed by piperidine (47 ml, 624 mmol). The mixture was stirred overnight at 80° C. under a reflux condenser. The solvents were removed under reduced pressure and the residue was diluted with 1M hydrochloric acid and extracted with dichloromethane (3×30 ml). The combined organic extracts were washed with brine, dried over anhydrous magnesium sulfate, filtered and evaporated to afford the desired product as a yellow oil (25 g, with residual solvent). $^1$H-NMR: δ (CDCl$_3$), 10.04 (1H, br s), 6.22 (1H, s), 5.57 (1H, d, J=1.3 Hz), 2.30 (2H, t, J=6.9 Hz), 1.38 (4H, m), and 0.91 (3H, t, J=7.2 Hz).

STEP 2: 4S-Benzyl-3-(2-butyl-acryloyl)-5,5-dimethyl-oxazolidin-2-one

2-Butyl acrylic acid (21.5 g, 168 mmol) was dissolved in dry THF (500 ml) and cooled to −78° C. under a blanket of argon. Triethylamine (30 ml, 218 mmol) and pivaloyl chloride (21 ml, 168 mmol) were added at such a rate that the temperature remained below −60° C. The mixture was stirred at −78° C. for 30 minutes, warmed to room temperature for 2 hours and finally cooled back to −78° C.

In a separate flask, 4S-benzyl-5,5-dimethyl-oxazolidin-2-one was dissolved in dry THF (500 ml) and cooled to −78° C. under a blanket of argon. n-Butyllithium (2.4 M solution in hexanes, 83 ml, 200 mmol) was added slowly and the mixture was stirred for 30 minutes at room temperature. The resulting anion was transferred via a cannula into the original reaction vessel. The mixture was allowed to warm to room temperature and was stirred overnight at room temperature. The reaction was quenched with I M potassium hydrogen carbonate (200 ml) and the solvents were removed under reduced pressure. The residue was partitioned between ethyl acetate and water. The organic layer was washed with brine, dried over anhydrous magnesium sulphate, filtered and concentrated under reduced pressure to give an orange oil. TLC analysis revealed the presence of unreacted chiral auxiliary in. addition to the required product. A portion of the material (30 g) was dissolved in dichloromethane and flushed though a silica pad to give pure title compound as a yellow oil (25.3 g). $^1$H-NMR; δ (CDCl$_3$), 7.31–7.19 (5H, m), 5.41 (2H, s), 4.51 (1H, dd, J=9.7, 4.2 Hz), 3.32 (1H, dd, J=14.2, 4.2 Hz), 2.82 (1H, dd, J=14.2, 9.7 Hz), 2.40–2.34 (2H, m), 1.48–1.32 (4H, m), 1.43 (3H, s), 1.27 (3H, s) and 0.91 (3H, t, J=7.1 Hz). Some chiral auxiliary was recovered by flushing the silica pad with methanol.

STEP 3: 4S-tert-Butyl-3-(2-butyl-acryloyl)-5,5-dimethyl-oxazolidin-2-one-2R-(tert-butoxyamino-methyl)-hexanamide 4S-Benzyl-3-(2-butyl-acryloyl)-5,5-dimethyl-oxazolidin-2-one (5 g, 15.92 mmol) was dissolved in ethanol (20 ml). O-tert-butylhydroxylamine hydrochloride (2.4 g, 19.10 mmol) and triethylamine (2.75 ml, 19.90 mmol) were then added and the reaction mixture stirred at 30° C. for 24 hours. Solvent was removed under reduced pressure and the residue dissolved in ethyl acetate and washed successively with 1 M hydrochloric acid, saturated sodium hydrogen carbonate and brine, dried over magnesium sulphate and filtered. Solvents were removed under reduced pressure to provide the title compound (5.62 g, 13.89 mmol, 87%) as a colourless oil. $^1$H-NMR: δ (CDCl$_3$), 7.29 (5H, m), 5.07 (1H, s), 4.51 (1H, dd, J=3.2, 10.0 Hz), 4.01 (1H, m), 3.25 (1H, dd, J=2.9,14.4 Hz), 3.03 (2H, m), 2.84 (1H, dd, J=4.3, 9.8 Hz), 1.69 (1H, m), 1.49 (2H, m), 1.34 (6H, s), 1.25 (3H, m), 1.13 (9H, s) and 0.87 (3H, t, J=6.9 Hz). LRMS:+ve ion 405 [M+H].

STEP 4: 2R-(tert-Butoxyamino-methyl)-hexanoic Acid 4S-tert-Butyl-3-(2-butyl-acryloyl)-5,5-dimethyl-oxazolidin-2-one-2R-tert-butoxyamino-methyl)-hexanamide (5.62 g, 13.89 mmol) was dissolved in THF (40 ml) and water (10 ml) and cooled to 0° C. and treated with lithium hydroxide (0.64 g, 15.28 mmol). The solution was stirred for 30 minutes at 0° C., then overnight at room temperature. The reaction was acidified to pH4 with 1 M citric acid and the solvents were removed. The residue was partitioned between dichloromethane and 1 M sodium carbonate. The basic aqueous layer was acidified to pH4 with 1M citric acid and extracted three times with ethyl acetate. The combined organic layers were dried over anhydrous magnesium sulfate, filtered and concentrated to provide the title compound as a colourless oil (2.0 g, 66%). $^1$H-NMR; δ (CDCl$_3$), 7.31 (2H, br s), 3.14 (1H, dd, J=9.1, 12.7 Hz), 2.99 (1H, dd, J=4.2, 12.7 Hz), 2.63 (1H, m), 1.65 (1H, m), 1.54 (1H, m), 1.29 (4H, m), 1.17 (9H, s) and 0.90 (3H, t, J=7.2 Hz).

STEP 5: 2R-[(tert-Butoxy-formyl-amino)-methyl]-hexanoic Acid

To a solution of 2R-(tert-butoxyamino-methyl)-hexanoic acid (4 g, 18.5 mmol) in dichloromethane (40 ml) at 0° C. was added formic acetic anhydride (4.1 ml, 46.25 mmol) and triethylamine (2.4 ml, 18.5 mmol). After 2 hours the solution was washed with water, saturated sodium hydrogen carbonate and brine, dried over anhydrous magnesium sulphate and filtered. The filtrate was evaporated to provide the title compound as an oil, which was taken on to Step 6 without further purification. LRMS: +ve ion 245 (M+H).

STEP 6: 2R-[(tert-Butoxy-formyl-amino)-methyl]-hexanoic Acid Pentafluorophenyl Ester 2R-[(tert-butoxy-formyl-amino)-methyl]-hexanoic acid (1.73 g, 7.06 mmol) was dissolved in dichloromethane (60 ml) and cooled to 0° C. Pentafluorophenol (1.43 g, 7.77 mmol) and EDC (1.5 g, 7.77 mmol) were added and the resulting solution stirred at 0° C. for 0.5 hours and room temperature for 4 hours. The solution was then washed with 1M sodium carbonate and brine, dried over magnesium sulphate and filtered. Solvents were removed under reduced pressure to provide the title compound as a colourless oil (2.6 g, 6.33 mmol, 90%). LRMS: +ve ion 412 (M+H).

EXAMPLE 1

2R-[(Formyl-hydroxy-amino)-methyl]-hexanoic acid (4,7,7-trimethyl-5-oxo-[1,4]thiazepan-6R-yl) amide

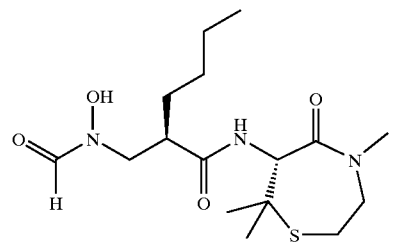

The title compound was prepared by the method described below (see also Scheme 2):

STEP A: 2R-tert-Butoxycarbonylamino-3-mercapto-3-methyl-butyric Acid

L-Penicillamine (15 g, 0.1 mol) was suspended in methanol (250 ml) and cooled to 0° C. Triethylamine (14 ml, 0.1 mol) and di-tert-butyl dicarbonate (24 g, 0.11 mol) in methanol (25 ml) were then added sequentially. The reaction mixture was allowed to stir at room temperature overnight, after which the solvents were removed under reduced pressure. The residue was dissolved in ethyl acetate (100 ml) and washed with 1N hydrochloric acid (100 ml), water (50 ml) and brine (50 ml), dried over anhydrous magnesium sulphate, filtered and evaporated to provide the title compound as a white solid. (28.1 g, including residual solvent). $^1$H-NMR; δ (CDCl$_3$), 9.13 (1H, brs), 5.52 (1H, d, J=9.9Hz), 4.34 (1H, d, J =9.3 Hz), 2.01 (1H, s), 1.53 (3H, s), 1.46 (9H, s) and 1.42 (3H, s).

STEP B: {1 R-[(2-Hydroxy-ethyl)-methyl-carbamoyl]-2-mercapto-2-methyl-propyl}-carbamic Acid tert-butyl Ester 2R-tert-Butoxycarbonylamino-3-mercapto-3-methyl-butyric acid (5 g, 20 mmol) was dissolved in DMF (30 ml) and the solution was cooled to 0° C. EDC (4.6 g, 24 mmol) and HOBt (3.25 g, 24 mmol) were added and the mixture was stirred for 15 minutes. N-(2-Hydroxy-ethyl)-N-methyl amine (1.16 ml, 20 mmol) was added and the reaction was allowed to warm to room temperature and was stirred overnight. The solvent was removed under reduced pressure and the residue was dissolved in dichloromethane, washed successively with 1 M hydrochloric acid, saturated sodium hydrogen carbonate and brine, dried over magnesium sulphate and filtered. Solvents were removed under reduced pressure and the residue was purified by flash column chromatography (silica gel, 5% methanol in dichloromethane) to provide the title compound as a colourless oil (3.58 g, 58%). $^1$H-NMR; δ (CDCl$_3$), 5.67 (1H, d, J=9.5 Hz), 5.55 (1H, d, J=8.7 Hz), 4.68 (2H, dd, J=9.7, 13.8 Hz), 3.79 (2H, m), 3.27 (3H, s), 2.77 (1 H, br s), 1.81 (1H, s), 1.44 (9H, s), 1.45 (3H, s) and 1.43 (3H, s).

STEP C: (4,7,7-Trimethyl-5-oxo-[1,4]thiazepan-6-yl)-carbamic Acid tert-Butyl Ester A solution of {1R-[(2-Hydroxy-ethyl)-methyl-carbamoyl]-2-mercapto-2-methyl-propyl}-carbamic acid tert-butyl ester (3 g, 9.8 mmol) in THF (100 ml) was treated with triphenylphosphine (3.28 g, 12.5 mmol) and diisopropylazodicarboxylate (2.45 ml, 12.5 mmol) and the resulting solution stirred at room temperature for 6 hours. Solvent was removed under reduced pressure and the residue purified by flash column chromatography (Biotage, 40% ethyl acetate in hexanes) to provide the title compound as a colourless oil (1.0 g, 35%). $^1$H-NMR; δ (CDCl$_3$), 5.83 (1H, d, J=7.8 Hz), 4.89 (1H, d, J=9.4 Hz), 4.00 (1H, dd, J=3.6, 9.6 Hz), 3.56 (1H, dd, J=5.4, 9.8 Hz), 3.04 (3H, s), 2.69 (1H, ddd, J=3.5, 5.5, 11.0 Hz), 1.44 (9H, s), 1.36 (3H, s) and 1.19 (3H, s). LRMS: +ve ion 289 [M+H].

STEP D: 6S-Amino4,7,7-trimethyl-[1,4]thiazepan-5-one

A solution of (4,7,7-trimethyl-5-oxo-[1,4thiazepan-6-yl) carbamic acid tert-butyl ester (1 g, 3.47 mmol) in dichloromethane (10 ml) and TFA (10 ml) was allowed to stand at 0° C. overnight. Solvents were removed under reduced pressure and the residue was dissolved in methanol (30 ml) and water (3 ml) and treated with Dowex400 resin to pH 8. The resin was removed by filtration and washed well with methanol. The filtrate and washings were evaporated to provide the title compound as a yellow oil (0.65 g, quant.). $^1$H-NMR; δ (CD$_3$OD), 3.94 (1H, s), 3.89 (1H, t, J=6.8 Hz), 3.62 (1H, dt, J=5.3, 15.5 Hz), 3.00 (3H, s), 2.82 (2H, t, J=5.3 Hz), 1.38 (3H, s) and 1.16 (3H, s). LRMS: +ve ion 189 [M+H].

STEP E: 2R-[(tert-Butoxy-amino)-methyl]-hexanoic Acid(4,7,7-trimethyl-5-oxo-[1,4]thiazepan-6R-yl) amide 2R-(tert-Butoxy-amino-methyl)-hexanoic acid (0.4 g, 1.85 mmol) was dissolved in DMF (30 ml) and the solution was cooled to 0° C. EDC (0.42, 2.18 mmol) and HOAt (25 mg, 0.185 mmol) were added and the mixture was stirred for 15 minutes. 6S-Amino4,7,7-trimethyl-[1,4]thiazepan-5-one (0.5 g, 1.85 mmol) was added and the reaction was allowed to warm to room temperature and was stirred overnight. The solvent was removed under reduced pressure and the residue was dissolved in dichloromethane, washed successively with 1 M hydrochloric acid, saturated sodium hydrogen carbonate and brine, dried over magnesium sulphate and filtered. Solvents were removed under reduced pressure and the residue was purified by flash column chromatography (Biotage, 50% ethyl acetate in hexanes) to provide the title compound as a colourless oil (160 mg, 22%). $^1$H-NMR; δ (CDCl$_3$), 6.99 (1H, d, J=8.2 Hz), 5.25 (1H, d, J=8.3 Hz), 5.00 (1H, s), 4.06 (1H, ddd, J=4.9, 10.5, 16.5 Hz), 3.53 (1H, dt, J=4.6, 16.8 Hz), 3.07 (1H,dd, J=7.1, 12.5 Hz), 3.04 (3H, s), 2.94 (1H,dd, J=4.6, 8.5 Hz), 2.84 (1H, dd, J=4.5, 9.5 Hz), 2.73 (1H, dt, J=3.9, 14.0 Hz), 1.55 (1H, m), 1.37 (3H, s), 1.28 (5H, m), 1.22 (3H, s), 1.16 (9H, s) and 0.87 (3H, t, J=7.7 Hz). LRMS: +ve ion 387 [M+H].

STEP F: 2R[(tertButoxy-formyl-amino)-methyl]-hexanoic Acid(4,7,7-trimethyl-5-oxo-[1,4]thiazepan-6R-yl) amide A solution of 2R[(tertButoxy-amino)-methyl]-hexanoic acid (4,7,7-trimethyl-5-oxo-[1,4]thiazepan-6R-yl) amide (1 60 mg, 0.41 mmol) in dichloromethane (5 ml) was treated with formic acetic anhydride (0.2 ml) and stirred for 5 hours. Solvents were removed under reduced pressure to provide the title compound as a colourless oil (180 mg, 97%). $^1$H-NMR; δ (CDCl$_3$, rotamers), 8.3 (1H, s), 7.17 (0.33H, d, J=7.4 Hz), 6.92 (0.66H, d, J=7.8 Hz), 5.31 (0.33H, d, J=9.4 Hz), 5.19 (0.66H, d, J=8.3 Hz), 4.03 (1H, m), 3.90 (1H, m), 3.68 (1H, m), 3.52 (1H, dt, J=5.7, 16.6 Hz), 3.03 (3H, s), 2.78 (3H, m), 1.56 (1H, m), 1.41 (2H, m), 1.35 (3H, s), 1.27 (9H, s), 1.23 (3H, m), 1.20 (3H, s) and 0.86 (3H, t, J=7.6 Hz). LRMS: +ve ion 416 [M+H].

STEP G: 2R-[(Formyl-hydroxy-amino)-methyl]-hexanoic Acid(4,7,7-trimethyl-5-oxo-[1,4]thiazepan-6R-yl) amide 2R-[(tert-Butoxy-formyl-amino)-methyl]-hexanoic acid (4,7,7-trimethyl-5-oxo-[1,4]thiazepan-6R-yl) amide (180 mg, 0.4 mmol) was dissolved in TFA (10 ml) and stirred at room temperature for 6 hours. Solvent was removed under reduced pressure, azeotroping several times with toluene. The title compound was purified using preparative HPLC (methanol:water, gradient method) as a white solid (80 mg, 0.22 mmol, 54%). $^1$H-NMR; δ (CDCl$_3$, (rotamers)), 8.39 (0.5H, s), 7.84 (0.5H, s), 7.19 (0.5H, d, J=8.3 Hz), 6.99 (0.5H, d, J=8.3 Hz), 5.28 (0.5H, d, J=8.2 Hz), 5.23 (0.5H, d, J=8.2 Hz), 4.05 (1.5H, m), 3.86 (0.5H, dd, J=9.9, 14.1 Hz), 3.52 (2H, m), 3.06 (1.5H, s), 3.04 (1.5H, s), 2.85 (1.5H, m), 2.74 (1.5H, m), 1.61 (1H, m), 1.43 (1H, m), 1.32 (1H, s), 1.30 (4H, m), 1.26 (2H, s), 1.21 (1H, s), 1.17 (2H, s), and 0.88 (3H, t, J=6.7 Hz). $^{13}$C-NMR; δ (CDCl$_3$, (rotamers)), 171.1, 59.4, 53.1, 52.8, 51.5, 48.4, 46.6, 45.2, 44.0, 36.7, 36.5, 30.3, 29.6, 27.5, 27.2, 24.0, 23.0 and 14.2. LRMS: +ve ion 360 [M+H], 382 [M+Na], –ve ion 358 [M–H].

Scheme 1

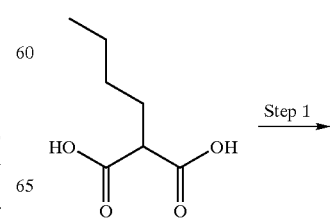

Step 1

15
-continued

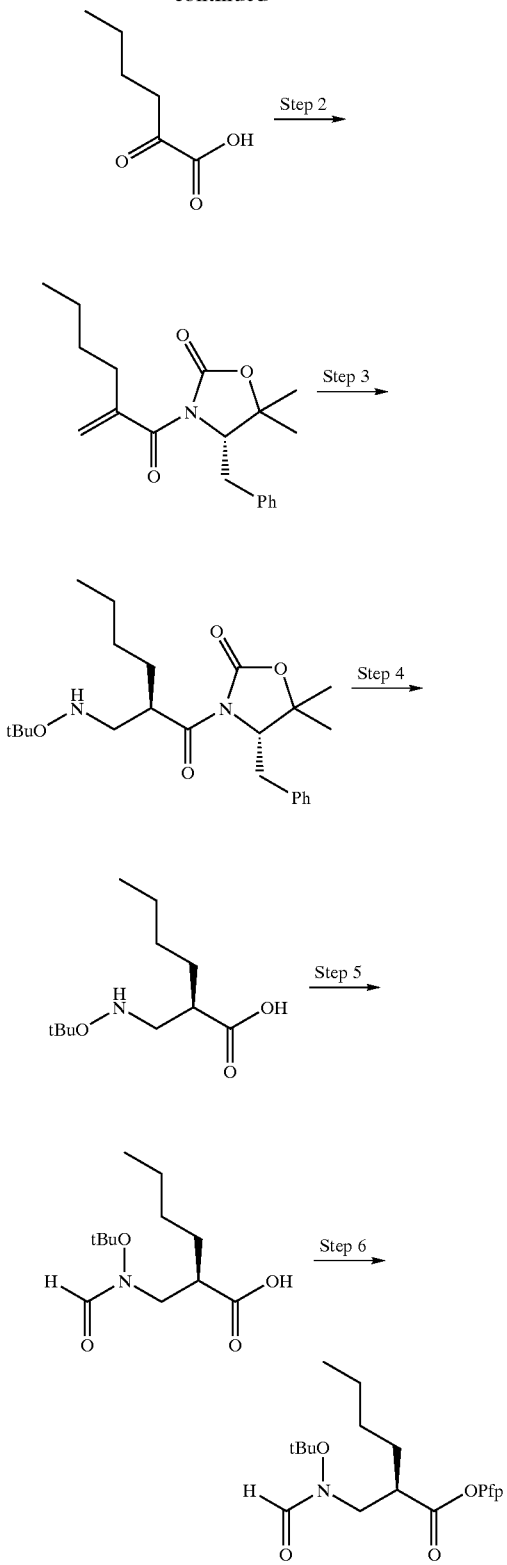

Reagents and conditions:
1. piperidine, HCHO, EtOH, 80° C., o/n;
2. tBuCOCl, Et₃N then 3-lithio-4-benzyl-5,5-dimethyl-oxazolidin-2-one;
3. H₂NOtBu.HCl, Et₃N, EtOH, 30° C., o/n;
4. LiOH, aq THF, 0° C. then 1M HCl.
5. HCOOAc, Et₃N, CH₂Cl₂;
6. Pentafluorophenol, EDC, CH₂Cl₂

16
Scheme 2

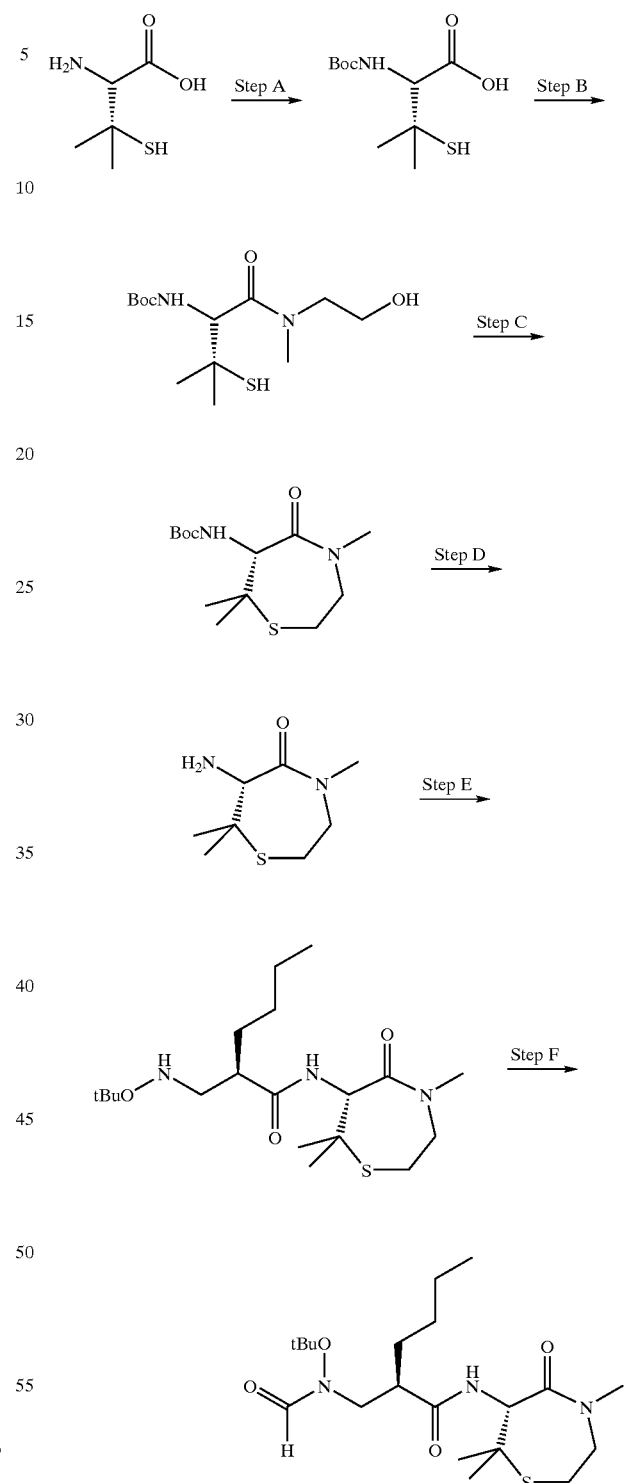

Reagents and conditions:
A Di-tert-butyl dicarbonate, Et₃N,MeOH;
B N-Methyl-2-aminoethanol, HOBT, EDC, DMF;
C PPh₃, diisopropylazodicarboxylate, THF;
D TFA, CH₂Cl₂;
E 2R-(tert-Butyloxyamino-methyl)-hexanoic acid, EDC, HOAt, DMF;
F HCOAc, CH₂Cl₂;
G TFA.

EXAMPLE 2

2-[(Formyl-hydroxy-amino)-methyl]-hexanoic Acid (5,5-Dimethyl-7-oxo-[1,4]oxathiepan-6-yl)-amide

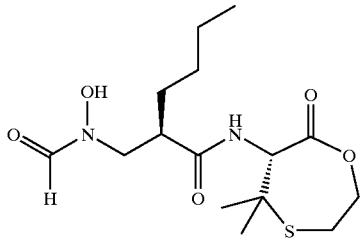

STEP A: 2S-tert-Butoxycarbonylamino-3-(2-hydroxy-ethylsulfanyl)-3-methyl-butyric Acid 2S-tert-Butoxycarbonylamino-3-mercapto-3-methyl-butyric acid (1 g, 4 mmol) was dissolved in a 1:1 mixture of ethanol and 1M sodium hydroxide solution (20 ml). 2-Bromoethanol (0.34 ml, 4.8 mmol) was then added and the resulting solution heated at 40° C. overnight. Ethanol was removed in vacuo and the residue diluted with water (10 ml), acidified to pH 1 with 1M hydrochloric acid and extracted with dichloromethane (3×10 ml). The combined organic layer was combined, washed with brine (10 ml), dried over anhydrous magnesium sulphate, filtered and evaporated to provide the title compound as a white gum (1.1 g, 3.75 mmol, 94%). $^1$H-NMR; δ (CDCl$_3$); 5.57 (1H, d, J =9.1 Hz), 5.38 (1H, br s), 4.40 (1H, d, J=9.2 Hz), 3.76 (2H, m), 2.83 (2H, t, J=5.8 Hz), 1.45 (9H, s), 1.42 (3H, s) and 1.35 (3H, s). LRMS: +ve ion 294 [M+H], 316 [M+Na], −ve ion 292 (M−H).

STEP B: (5,5-Dimethyl-7-oxo-[1,4]oxathiepan-6S-yl)-carbamic Acid tert-Butyl Ester A solution of 2S-tert-butoxycarbonylamino-3-(2-hydroxy-ethylsulfanyl)-3-methyl-butyric acid (1.1 g, 3.75 mmol) and ethyl chloroformate (0.4 ml, 4.12 mmol) in dichloromethane was cooled to 0° C. and treated dropwise with triethylamine (0.57 ml, 4.12 mmol) and dimethylaminopyridine (46 mg, 0.375 mmol). The resulting solution was stirred at 0° C. for 0.5 hours then diluted with dichloromethane (15 ml), washed successively with 1 M hydrochloric acid, saturated sodium hydrogen carbonate and brine, dried over magnesium sulphate and filtered. Solvents were removed in vacuo to provide the title compound (0.86 g, 3.12 mmol, 83%) as a colourless oil. $^1$H-NMR; δ (CDCl$_3$); 5.59 (1H, d, J=8.1 Hz), 5.03 (1H, d, J=8.6 Hz), 4.65 (2H, m), 3.05 (1H, ddd, J=3.7, 8.4, 15.7 Hz), 2.79 (1H, ddd, J=2.3, 4.8, 15.8 Hz), 1.45 (9H, s), 1.39 (3H, s) and 1.27 (3H, s) and 2.27 (3H, s). LRMS: +ve ion 276 [M+H], 298 [M+Na].

STEP C: 6S-Amino-5,5-dimethyl-[1,4]oxathiepan-7-one

A solution of (5,5-dimethyl-7-oxo-[1,4]oxathiepan-6S-yl)-carbamic acid tert-butyl ester (0.86 g, 3.12 mmol) in 5% aqueous trifluoroacetic acid (20 ml) was allowed to stand at 0° C. for 16 hours. Solvents were removed in vacuo, azeotroping with toluene, then the residue dissolved in 10% aqueous methanol (30 ml) and adjusted to pH 8 with Dowex 1×8 400 resin. This was filtered and concentrated under reduced pressure to provide the title compound as a colourless gum (0.72 g, 4 mmol, 100%). $^1$H-NMR; δ (CDCl$_3$); 4.71 (1H, ddd, J=2.7, 5.5, 12.9 Hz), 4.54 (1H, ddd, J=2.0, 8.9, 14.9 Hz), 4.33 (1H, s 3.02 (1H, ddd, J=2.8, 8.9, 15.9 Hz), 2.81 (1H, ddd, J=1.9, 5.7, 11.6 Hz), 2.33 (2H, s), 1.46 (3H, s) and 1.34 (3H, s).

STEP D: 2-[(Formyl-hydroxy-amino)-methyl]-hexanoic Acid(5,5-Dimethyl-7-oxo-[1,4]oxathiepan-6-yl)-amide A solution of 6S-amino-5,5-dimethyl-[1,4]oxathiepan-7-one (320 mg, 1.83 mmol) and 2R-[(tert-butoxy-formyl-amino)-methyl]-hexanoic acid pentafluorophenyl ester (0.5 g, 1.22 mmol) in DMF (5 ml) was stirred at room temperature for 5 days. DMF was removed in vacuo and the residue dissolved in dichloromethane (30 ml), washed successively with 1 M hydrochloric acid, saturated sodium hydrogen carbonate and brine, dried over magnesium sulphate and filtered. Solvents were removed under reduced pressure and the residue dissolved trifluoroacetic acid (10 ml) and stirred at room temperature for 6 hours. Solvent was removed in vacuo, azeotroping with toluene, and the title compound was purified using preparative HPLC (methanol:water, gradient method) (80 mg, 0.22 mmol, 54%) as a white solid. $^1$H-NMR; δ (CDCl$_3$, (rotamers)), 8.36 (0.33H, s), 7.85 (0.66H, s), 7.18 (0.66H, d, J=7.3 Hz), 7.10 (0.33H, d, J=7.9 Hz), 5.41 (1H, d, J=8.5 Hz), 4.69 (2H, m), 3.75 (2H, m), 3.42 (1H, dd, J=4.0, 14.2 Hz), 3.09 (1H, m), 2.94 (1H, m), 2.80 (2H, m), 1.65 (1H, m), 1.35 (3H, s), 1.32 (5H, m), 1.30 (3H, s), and 0.89 (3H, t, J=6.5 Hz). $^{13}$C-NMR; δ (CDCl$_3$ (rotamers)), 173. 8, 172.8, 71.6, 71.3, 61.2, 60.9, 52.3, 49.1, 46.0, 44.7, 43.4, 43.2, 30.4, 30.2, 29.8, 28.8, 27.5, 26.5, 23.0 and 14.3. LRMS: +ve ion 347 (M+H), 369 (M+Na), −ve ion 345 (M−H).

The compounds of Examples 3 to 5 were prepared by parallel synthesis in solution from 2R-tert-butyloxyamino-methyl)-hexanoic acid pentafluorophenyl ester and penicillamine derived [1,4]oxathiepan amines. The requisite amines were prepared as outlined in Scheme 3 and as described in detail below.

STEP A: (2,2-Dimethyl4-oxo-thietan-3-yl)-carbamic Acid tert-Butyl Ester 2S-tert-Butoxycarbonylamino-3-mercapto-3-methyl-butyric acid (8 g, 32.10 mmol) was dissolved in dichloromethane (300 ml) and cooled to 0° C. Pentafluorophenol (6.5 g, 35.31 mmol) and EDC (7.4 g, 38.52 mmol) were then added and the resulting solution allowed to warm to room temperature and stirred for 2 hours, washed successively with 1 M hydrochloric acid, 1M sodium carbonate and brine, dried over magnesium sulphate and filtered. Solvents were removed in vacuo to provide the title compound as a white solid (7.45 g, 100%). $^1$H-NMR; δ (CDCl$_3$); 5.41 (1H, d, J=8.4 Hz), 5.30 (1H, br s), 1.83 (3H, s), 1.64 (3H, s) and 1.45 (9H, s).

STEPS B–D:

(2,2-Dimethyl4-oxo-thietan-3-yl)-carbamic acid tert-butyl ester (0.62 g, 2.7 mmol) and the required 2-hydroxy amine (2-hydroxymethylpiperidine for Example 3, N-ethyl-ethanolamine for Example 4 or N-propyl-ethanolamine for Example 5; 2.7 mmol) were dissolved in DMF (5 ml) and stirred at ambient temperature over night then concentrated in vacuo. The residue was dissolved in tetrahydrofuran (20 ml) and tri-n-butyl phosphine (1 ml, 4.05 mmol) added and the solution cooled to 0° C. 1,1'-(Azodicarbonyl) dipiperidine (1 g, 4.05 mmol) was the added and the solution stirred at 0° C. for 5 minutes and at ambient temperature for 4 hours, then diluted with hexane (5 ml), filtered through a cartridge containing a plug of silica and concentrated in vacuo. The residue was dissolved in 5% aqueous TFA (20 ml) and allowed to stand at 0° C. overnight then concentrated in vacuo, azeotroping with toluene. The residue was dissolved in dichloromethane (20 ml) and extracted into water (3×10 ml). The aqueous solution was adjusted to pH 8 with 1M sodium carbonate and extracted with dichloromethane, dried over magnesium sulphate and filtered. Solvents were removed in vacuo to provide the required amines. A solution of the amine (1.1 equivalent) and 2R-tert-butyloxyamino-methyl)-hexanoic acid pentafluorophenol ester (1 equivalent) in dichloromethane (5 ml) was stirred at ambient temperature overnight.

The solution was then treated with carbonate resin (3 mmol/g, 3 equivalents) for 1 hour, filtered and treated with sulphonic acid resin (1 mmol/g, 3 equivalents) for a further 1 hour. The suspension was filtered and concentrated to dryness in vacuo. The residue was dissolved in trifluoroacetic acid (10 ml) and stirred at ambient temperature for 6 hours then concentrated in vacuo. Final compounds were purified using preparative HPLC (methanol: water, gradient method).

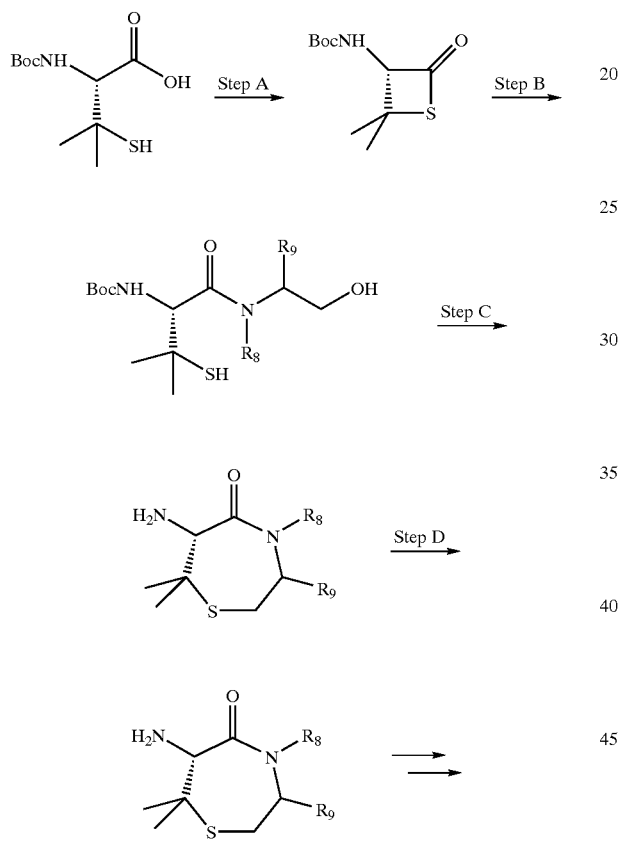

Reagents and conditions:
A Pfp, EDC, DCM;
B 2-Hydroxy amine, DMF;
C P($^n$Bu)$_3$, ADDP, THF;
D TFA then NaHCO$_3$

EXAMPLE 3

2-[(Formyl-hydroxy-amino)-methyl]-hexanoic acid (7,7-dimethyl-5-oxo-octahydro-8-thia-4a-aza-benzocyclohepten-6-yl)-amide

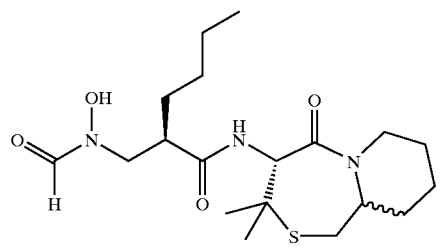

Yellow oil, 4.6 mg. LRMS +ve ion: 400 (M+H).

EXAMPLE 4

2-[(Formyl-hydroxy-amino)-methyl]-hexanoic acid (4-ethyl-7,7-dimethyl-5-oxo-[1,4]thiazapan-6-yl)-amide

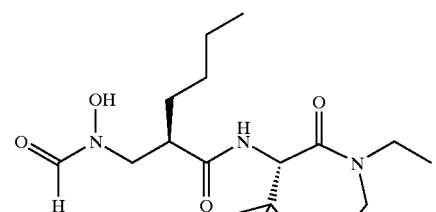

Colourless oil, 24 mg. LRMS +ve ion: 374 (M+H).

EXAMPLE 5

2-[(Formyl-hydroxy-amino)-methyl]-hexanoic acid (4-propyl-7,7-dimethyl-5-oxo-[1,4]thiazapan-6-yl)-amide

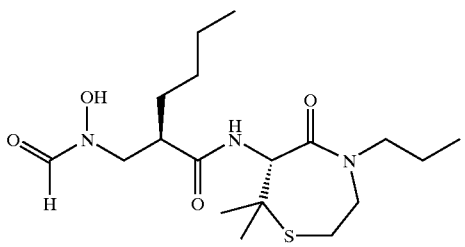

Yellow oil, 40 mg. LRMS +ve ion: 388 (M+H), −ve ion: 386 (M−H).

EXAMPLE 6

2R-[(Formyl-hydroxy-amino)methyl]-hexanoic acid (1benzyl-2-oxo-piperidin-3S-yl) amide

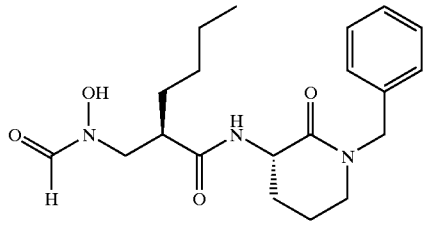

Step A: 5-Benzylamino-2S-benzyioxycarbonylamino-pentanoic Acid

Benzaldehyde (0.42 ml, 4.25 mmol) was added to a stirred suspension of 5-amio-2S-benzyloxycarbonylamino-pentanoic acid (1.0 g, 3.75 mmol), triethylamine (0.62 ml, 4.5 mmol) and magnesium sulfate (0.96 g, 8.1 mmol) in methanol (10 ml) and the stirring continued at room temperature overnight. The reaction mixture was then filtered and concentrated in vacuo. The residue was dissolved in methanol, cooled in an ice bath and sodium cyanoborohydride (0.28 g, 7.5 mmol) was added portion-wise. After 2 hours, acetone (30 ml) was added to quench the reaction and the reaction mixture was concentrated in vacuo to leave the crude title compound as brown solid (1.6 g) which was taken on to the next step without further purification.

Step B: (1-Benzyl-2-oxo-piperidin-3S-yl)-carbamic Acid Benzyl Ester

5-Benzylamino-2S-benzyloxycarbonylamino-pentanoic acid was diluted DMF (16 ml) and cooled in an ice bath. HOBt (51 mg, 0.37 mmol) and EDC (0.75 g, 3.9 mmol) were added to the stirred solution and the stirring continued for 60 h. The reaction mixture was concentrated in vacuo and the residue was dissolved in ethyl acetate. The organic extract was washed with 1M hydrochloric acid (15 ml), 1M sodium carbonate (15 ml), brine (15 ml), dried over magnesium sulphate and concentrated under reduced pressure. Silica column chromatography (dichloromethane: methanol 98:2 to 80:20) gave the pure title compound (0.3 g, 25%). $^{1}$H-NMR; δ (CDCl$_3$) 7.30 (10H, m), 5.85 (1H, s), 5.12 (2H, s), 4.64 (2H, m), 4.15 (1H, m), 3.24 (2H, m), 1.88–1.52 (4H, m). LRMS: +ve ion 339 [M+H].

Step C: 3S-Amino-1Benzyl-piperidin-2-one

Palladium on charcoal (10%) was added to a stirred solution of (1-benzyl-2-oxo-piperidin-3S-yl)-carbamic acid benzyl ester (0.29 g, 0.86 mmol) in ethanol (40 ml) under argon. H$_2$ was bubbled through the suspension for 2 h. The mixture was purged with argon before the catalyst was removed by filtration. The solvent was removed in vacuo to afford the title compound as a colourless oil (0.17 g, 98%). $^{1}$H-NMR: δ (CDCl$_3$) 7.26 (5H, m), 4.49 (2H, m) 3.52 (1H, m), 3.23 (2H, m), 2.26–1.73 (4H, m). LMRS: +ve ion 205 [M+H]

Step D: 2R-[(Benzyloxy-amino-formyl)-methyl]-hexanoic Acid(1-benzyl-2-oxo-piperidin-3S-yl) amide To a solution of 2R-[(benzyloxy-formyl-amino)-methyl]-hexyl pentafluorophenyl ester (155 mg, 0.81 mmol) in dichloromethane (4 ml) was added 3S-amino-1-benzyl-piperidin-2-one (240 mg, 0.54 mmol) and the reaction mixture was stirred at 30° C. for 48 h. Purification was effected by removing excess amine and pentafluorophenol using scavenger resins. The pentafluorophenol was removed using a three fold excess (0.46 g, 1.62 mmol) of A-26 carbonate resin (3.5 mmol loading). The resin was added to the reaction mixture and agitated for 3 h, after which time it was removed by filtration. The excess amine was removed using a five fold excess (2.7 g, 2.76 mmol) of methylisocyanate polystyrene resin (1.2 mmol loading). The resin was added to the reaction mixture and agitated for 3 h, after which time it was removed by filtration and the solvent was removed in vacuo. Silica column chromatography (dichloromethane:methanol 99:1 to 97:3) gave the pure title compound (140 mg, 57%). 1H-NMR; δ (CDCl$_3$, rotamers) 8.15 (0.5H, s), 7.87 (0.5H, s), 7.36 (1 OH, m), 6.61 (1H, br.s), 4.98–4.47 (4H, m), 4.28 (1H, m), 3.78 (1H, s), 3.22 (2H, m), 2.53 (2H, m), 1.82–1.29 (10H, m), 0.88 (3H, s). LRMS: +ve ion 466 [M+H]

Step E: 2R-[(Formyl-hydroxy-amino)-methyl]-hexanoic Acid(1-benzyl-2-oxo-piperidin-3S-yl) amide 2R-[(Benzyloxy-amino-formyl)methyl]-hexanoic acid (1-benzyl-2-oxo-piperidin-3S-yl) amide (140 mg, 0.30 mmol) was dissolved in ethanol (10 ml) and placed under a blanket of argon. Palladium on charcoal (14 mg, 10% weight) was added and the mixture was stirred vigorously as hydrogen gas was bubbled through the system during 3 h. The flask was purged with argon before removing the catalyst by filtration. The filtrate was concentrated under reduced pressure to provide the title compound as a colourless oil (110 mg, 98%). $^{1}$H-NMR; δ (CDCl$_3$, rotamers), 8.42 (0.5H, s) 7.80 (0.5H, s), 7.32 (5H, m), 4.73–4.47 (2H, m), 4.24 (0.5H, m), 3.93 (1H, q), 3.61–3.34 (1H, s), 3.24 (2H, m), 2.78–2.43 (2H, m), 2.23–1.24 (10H, m), 0.89 (3H, t, J=6.3 Hz). $^{13}$C-NMR; δ (CDCl$_3$, rotamers), 174.3, 169.9, 136.1, 128.7, 127.8, 127.5, 51.9, 50.9, 50.8, 47.1, 45.7, 29.3, 26.9, 22.5, 21.5, 20.7 and 13.8. LRMS: +ve ion 376 [M+H].

EXAMPLE 7

2R-[(Formyl-hydroxy-amino)-methyl]-hexanoic acid (2-oxo-azepan-3S-yl)-amide

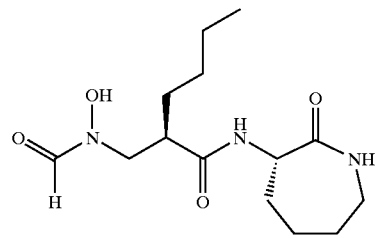

The title compound was prepared in an analogous fashion to Example 6, from commercially available 3S-aminohexahydro-2-azepinone.

Colourless oil. $^{1}$H-NMR; δ (CDCl$_3$, rotamers), 8.85 (0.5H, s) 7.79 (0.5H, s), 4.51 (1H, m), 3.71 (1H, m), 3.46–3.19 (3H, m), 2.86 (1H, t, J=8.5 Hz), 1.98–1.66 (6H, m), 1.32–1.17 (6H, m), 0.89 (3H, t, J=6.6 Hz). $^{13}$C-NMR; δ (CDCl$_3$, rotamers), 177.2, 172.3, 157.9, 53.7, 52.7, 45.6, 42.7, 31.4, 30.1, 29.4, 29.0, 28.5, 23.2 and 14.3. LMRS: +ve ion 300 [M+H].

EXAMPLE 8

2R-[(Formyl-hydroxy-amino)-methyl]-hexanoic acid (2,9-dioxo-1,8 diaza-cyclotetradec-3S-yl)-amide

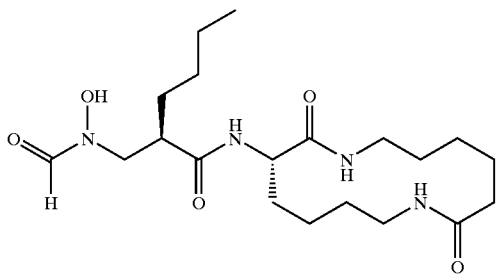

The title compound was prepared by the method outlined in Scheme 4 and is described in detail below.

Scheme 4

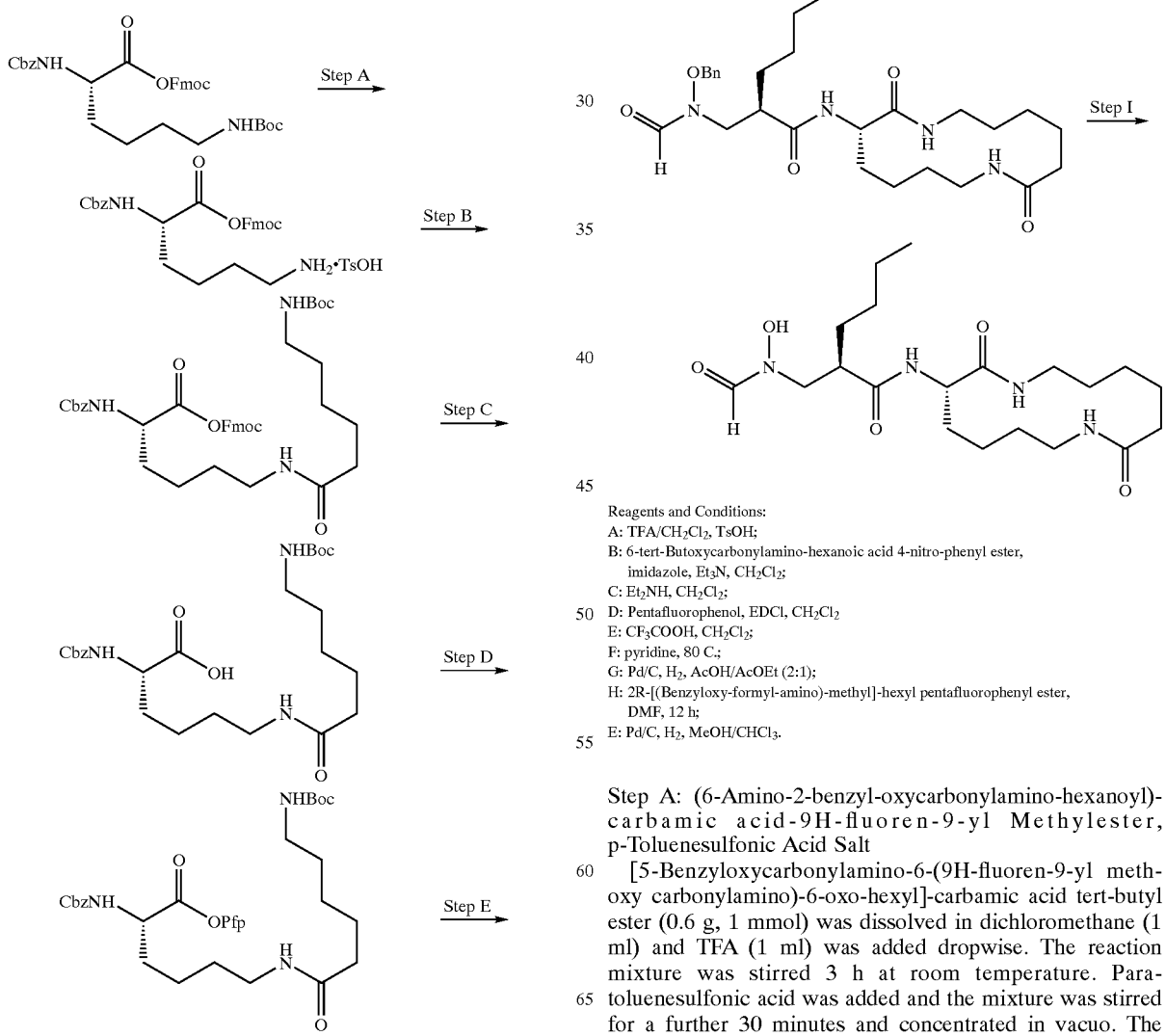

Reagents and Conditions:
A: TFA/CH$_2$Cl$_2$, TsOH;
B: 6-tert-Butoxycarbonylamino-hexanoic acid 4-nitro-phenyl ester, imidazole, Et$_3$N, CH$_2$Cl$_2$;
C: Et$_2$NH, CH$_2$Cl$_2$;
D: Pentafluorophenol, EDCl, CH$_2$Cl$_2$
E: CF$_3$COOH, CH$_2$Cl$_2$;
F: pyridine, 80 C.;
G: Pd/C, H$_2$, AcOH/AcOEt (2:1);
H: 2R-[(Benzyloxy-formyl-amino)-methyl]-hexyl pentafluorophenyl ester, DMF, 12 h;
E: Pd/C, H$_2$, MeOH/CHCl$_3$.

Step A: (6-Amino-2-benzyl-oxycarbonylamino-hexanoyl)-carbamic acid-9H-fluoren-9-yl Methylester, p-Toluenesulfonic Acid Salt

[5-Benzyloxycarbonylamino-6-(9H-fluoren-9-yl methoxy carbonylamino)-6-oxo-hexyl]-carbamic acid tert-butyl ester (0.6 g, 1 mmol) was dissolved in dichloromethane (1 ml) and TFA (1 ml) was added dropwise. The reaction mixture was stirred 3 h at room temperature. Para-toluenesulfonic acid was added and the mixture was stirred for a further 30 minutes and concentrated in vacuo. The residue was triturated with diethyl ether and seeded. After 2 h at 4° C., the white solid was collected by filtration. (0.49 g, 78%) $^1$H-NMR: δ (CDCl$_3$) 7.77–7.27 (17H, m), 6.15 (1H, brs), 5.67 (1H, d, J=7.8 Hz), 5.06 (2H, m), 4.52–4.11 (5H, m), 2.75 (2H, br.s), 2.26 (3H, s) and 1.25–1.14 (6H, m), $^{13}$C-NMR; δ (CDCl$_3$) 172.1, 156.0, 143.4, 143.2, 141.2, 140.8, 136.2, 128.0, 124.8, 119.8, 66.8, 66.6, 53.8, 46.7, 39.3, 31.3, 26.9, 21.8 and 21.2.

Step B: [2-Benzyloxycarbonylamino-6-(6-tert-butoxycarbonylamino-hexanoylamino)-hexanoyl]-carbamic acid 9H-fluoren-9-yl methyl ester.

To a solution of (6-amino-2-benzyl-oxycarbonylamino-hexanoyl)-carbamic acid 9H-fluoren-9-yl methylester, tosic acid salt (0.252 g, 0.4 mmol) and 6-tert-butoxycarbonylamino-hexanoic acid 4-nitro-phenyl ester (0.14 g, 0.4 mmol) in dichloromethane (3 ml) was added imidazole (0.03 g, 0.44 mmol). After stirring for 1 h at room temperature, a yellow colour was observed, then triethylamine (55 μl, 0.4 mmol) was added. The reaction mixture was stirred for 12h. The mixture was diluted and washed with 1M hydrochloric acid (10 ml), 0.5M sodium carbonate (10 ml), brine (10 ml), dried over anhydrous magnesium sulphate and concentrated under reduced pressure. Flash column chromatography (dichloromethane-methanol, 9:1) gave a light foam (0.203 g, 76%). $^1$H-NMR; δ (CDCl$_3$) 7.77–7.26 (13H, m), 5.77 (1H, br.s), 5.60 (1H, d, J=8.0 Hz), 5.10 (2H, s), 4.65 (1H, br.s), 4.49 (2H, m), 4.35 (1H, br.s), 4.19 (1H, m), 3.18(2H, m), 3.15 (2H, m), 2.10 (2H, t, J=7.5 Hz), and 1.68–1.18 (21H, m).

Step C: [2-Benzyloxycarbonylamino-6-(6-tert-butoxycarbonylamino-hexanoylamino)-hexanoic Acid.

[2-Benzyloxycarbonylamino-6-(6-tert-butoxycarbonyl-amino-hexanoylamino)-hexanoyl]-carbamic acid 9H-fluoren-9-yl methyl ester was dissolved in dichloromethane containing 5% of diethylamine (2 ml) and stirred for 6 h at room temperature. The reaction mixture was concentrated in vacuo. Flash column chromatography (dichloromethane-methanol-acetic acid 18:1:1) gave the pure product (0.13 g, 87%). $^1$H-NMR; δ (CDCl$_3$) 9.00–8.75 (1H, br.s), 7.26 (5H, s), 6.31 (1H, br.s), 5.80 (1H, d, J=7.8 Hz), 5.12 (2H, s), 4.85 (1H, br.s), 4.35 (1H, m), 3.11 (2H, m), 3.05 (2H, m), 2.17 (2H, t, J=7.4 Hz), and 1.95–1.20 (21H, m).

Step D: [2-Benzyloxycarbonylamino-6-(6-tert-butoxycarbonylamino-hexanoyfamino)-hexanoic Acid Pentafluoro-phenyl Ester.

A solution of [2-benzyloxycarbonylamino-6-(6-tert-butoxycarbonylamino-hexanoylamino)-hexanoic acid (0.13 g, 0.26 mmol) and pentafluorophenol (0.1 g, 0.54 mmol) in dichloromethane (5 ml) was stirred and cooled in an ice bath during the addition of EDC (55 mg, 0.29 mmol). The stirring was continued at room temperature for 3 h. The mixture was washed twice with 1M hydrochloric acid (10 ml), 0.5M sodium carbonate (10 ml), brine (10 ml), dried over anhydrous magnesium sulphate and concentrated under reduced pressure. The resulting gum was triturated with hexane to give an amorphous solid (0.13 g, 75%). $^1$H-NMR; δ (CDCl$_3$) 7.32 (5H, s), 6.00 (2H, br.t and br.d), 5.12 (2H, s), 4.63 (2H, m), 3.23 (2H, m), 3.03 (2H, m), 2.12 (2H, t, J=7.5 Hz), and 1.65–1.21 (21H, m).

Step E: 6-(6-Amino-hexanoylamino)-2-benzyloxycarbonylamino-hexanoic Acid Pentafluoro-phenyl-ester, Trifluoroacetic Acid Salt.

[2-Benzyloxycarbonylamino-6-(6-tert-butoxycarbonyl-amino-hexanoylamino)-hexanoic acid pentafluorophenyl ester (130 mg, 0.2 mmol) was dissolved in dichloromethane (3 ml) and TFA (0.5 ml) was added dropwise. The reaction mixture was stirred for 2 h at room temperature and concentrated in vacuo to leave the crude title compound which was taken on to the next step without further purification.

Step F: (2,9-Dioxo-1,8-diaza-cyclotetradec-3S-yl)-carbamic Acid Benzyl Ester 6-(6-Amino-hexanoylaminoy2-benzyloxycarbonyl-amino-hexanoic acid pentafluorophenyl ester trifluoroacetic acid salt was dissolved in pyridine and heated to 80° C. (64 mg, 86%).

Step G: 3S-Amino-1,8-diaza-cyclotetradecane-2,9-dione

Palladium on charcoal (10%, 50 mg) was added to a stirred suspension of (2,9-dioxo-1,8-diaza-cyclotetradec-3-S-yl)-carbamic acid benzyl ester (500 mg, 1.33 mmol) in aceic acid-ethyl acetate 2:1 (6 ml) under argon. H$_2$ was bubbled through the suspension for 2 h and left under an atmosphere of hydrogen. The flask was purged with argon before the catalyst was removed by filtration. The filtrate was concentrated under reduced pressure to provide the title compound as a yellow oil (254 mg, 98%). $^1$H-NMR; δ (CD$_3$OD) 3.69–3.40 (3H, m), 3.04–2.90 (2H, br.m), 2.25–2.16 (2H, br.m), 1.94–1.12 (12H, br.m). LRMS: +ve ion 242 [M+H]

Step H: 2R-abenzycoxy-amino-formyl)-methyl]-hexanoic acid (2,9-dioxo-1,8-diaza-cyclotetradec-3S-yl)-amide To a solution of 2R-[(benzyloxy-formyl-amino)-methyl]-hexyl pentafluorophenyl ester (233 mg, 0.52 mmol) in DMF (10 ml) was added 3S-amino-1.8-diaza-cyclotetradecane-2, 9-dione (254 mg, 1.05 mmol) and the reaction mixture was stirred at room temperature for 12 h. The reaction mixture was concentrated in vacuo and the residue dissolved in methanol-dichiloromethane 1:1(10 ml). Purification was effected by removing excess amine and pentafluorophenol using scavenger resins. The pentafluorophenol was removed using a three fold excess (0.44 g, 1.56 mmol) of A-26 carbonate resin (3.5 mmol loading). The resin was added to the reaction mixture and agitated for 3 h, after which time it was removed by filtration. The excess amine was removed using a five fold excess (2.6 g, 2.60 mmol) of methylisocy-anate polystyrene resin (1.2 mmol loading). The resin was added to the reaction mixture and agitated for 3 h, after which time it was removed by filtration and the solvent was removed in vacuo. The resulting yellow solid was triturated with MeOH to give by filtration the title compound as a colourless solid (100 mg, 38%).$^1$H-NMR; δ (CDCl$_3$, rotamers) 8.14 (0.5H, s), 7.87 (0.5H, s), 7.40 (5H, m), 4.91 (2H, m), 4.28 (1H, m), 3.77–3.37 (3H, m), 2.95 (2H, m), 2.70 (H, m), 2.19 (2H, m), 1.69–1.27 (18H, m), 0.88 (3H, t, J=6.9 Hz). LRMS: +ve ion 503 [M+H].

Step I: 2R-[(formyl-hydroxy-amino)-methyl]-hexanoic Acid(2,9-dioxo-1,8-diaza-cyclotetradec-3S-yl)-amide 2R-[(Benzyloxy-aminoformyl)-methyl]-hexanoic acid (2,9-dioxo-1,8-diaza-cyclotetradec-3S-yl)-amide (100 mg, 0.20 mmol) was dissolved in methanol-chloroform 1:1 (10 ml) and placed under a blanket of argon. Palladium on charcoal (10 mg, 10% weight) was added and the mixture was stirred vigorously as hydrogen gas was bubbled through the system for 2h. The flask was purged with argon before the catalyst was removed by filtration. The filtrate was concentrated under reduced pressure to provide the title compound as a colourless solid (80 mg, 97%). $^1$H-NMR; δ (CD$_3$OD, rotamers), 8.25 (0.4H, s), 8.15 (1H, m), 7.97 (1H, m), 7.82 (0.6H, s), 4.27 (1H, m), 3.77–3.37 (4H, m), 2.99–2.85 (3H, m), 2.18 (2H, m), 1.66–1.31 (18H, m), 0.89 (3H, t, J=6.8 Hz). $^{13}$C-NMR; δ (CDCl$_3$, rotamers), 55.3, 53.9, 47.8, 40.2, 39.8, 36.9, 33.5, 31.2, 30.7, 30.2, 26.9, 26.8, 24.1, 23.7 and 14.6. LMRS: +ve ion 425 [M+Na], 413 [M+H].

EXAMPLE 9

2R-[(Formyl-hydroxy-amino)-methyl]-hexanoic Acid(2-oxo-azacyclotridec-3R,S-yl)-amide

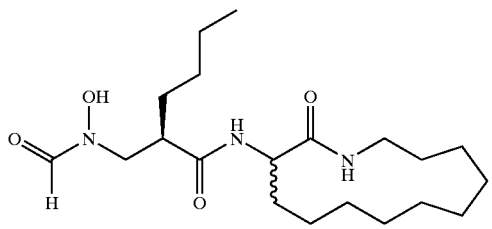

The title compound was prepared in an analogous fashion via steps H and I in scheme 6 from 3-amino-azacyclotnidecan-2one (Patent; Ajinomoto Co. Inc.; DE 1955038; Chem. Abstr.; EN; 73; 34829). Colourless solid.

$^1$H-NMR; δ (CDCl3, rotamers, mixture of diastereoisomers), 8.39 (0.3H, s), 8.38 (0.2H, s), 7.81 (0.3H, s), 7.79 (0.2H, s), 6.80–5.98 (2H, br.m) 4.47 (1H, m), 3.76 (2H, m), 3.50 (1H, m), 2.96–2.65 (2H, m), 1.71–1.04 (24H, m), 0.88 (3H, t, J=6.1 Hz). $^{13}$C-NMR; δ (CDCl$_3$, rotamers), 175.5, 174.0, 53.6, 51.8, 44.8, 39.4, 31.9, 31.6, 29.4, 29.3, 28.9, 26.7, 26.3, 24.7, 24.5, 23.8, 22.6 and 22.2. LMRS: +ve ion 384 [M+H].

EXAMPLE 10

2R-[(Formyl-hydroxy-amino)-methyl]-hexanoic Acid[4-methyl-5-oxo-1-(4-trifluoromethyl-benzenesulfonyl)-[1,4]diazepan-6S-yl]-amide

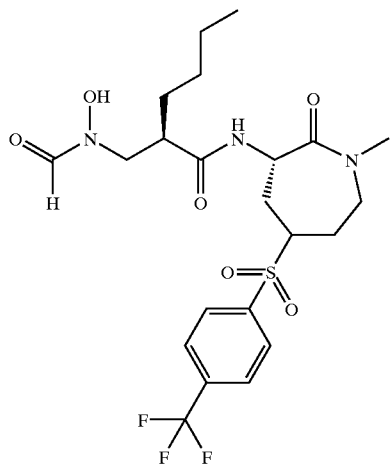

The compound was prepared according to the method described below (see also Scheme 5):

Scheme 5

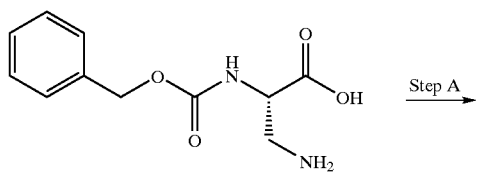 Step A →

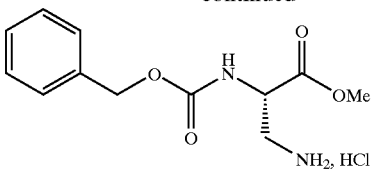 Step B →

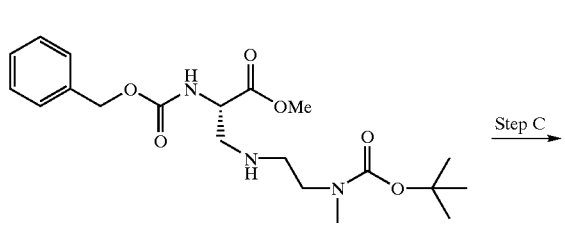 Step C →

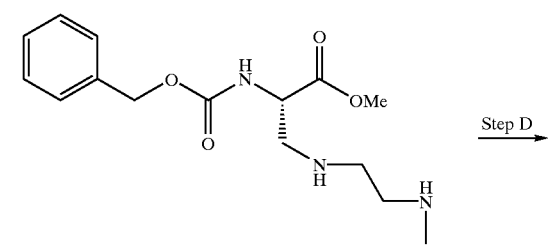 Step D →

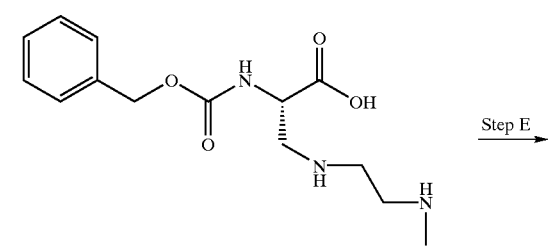 Step E →

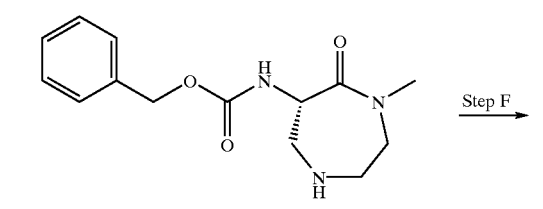 Step F →

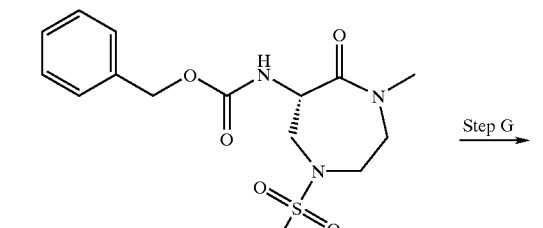 Step G →

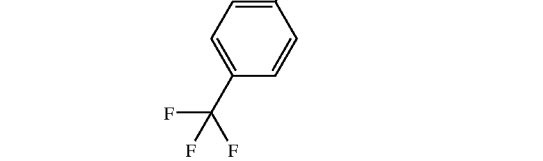

-continued

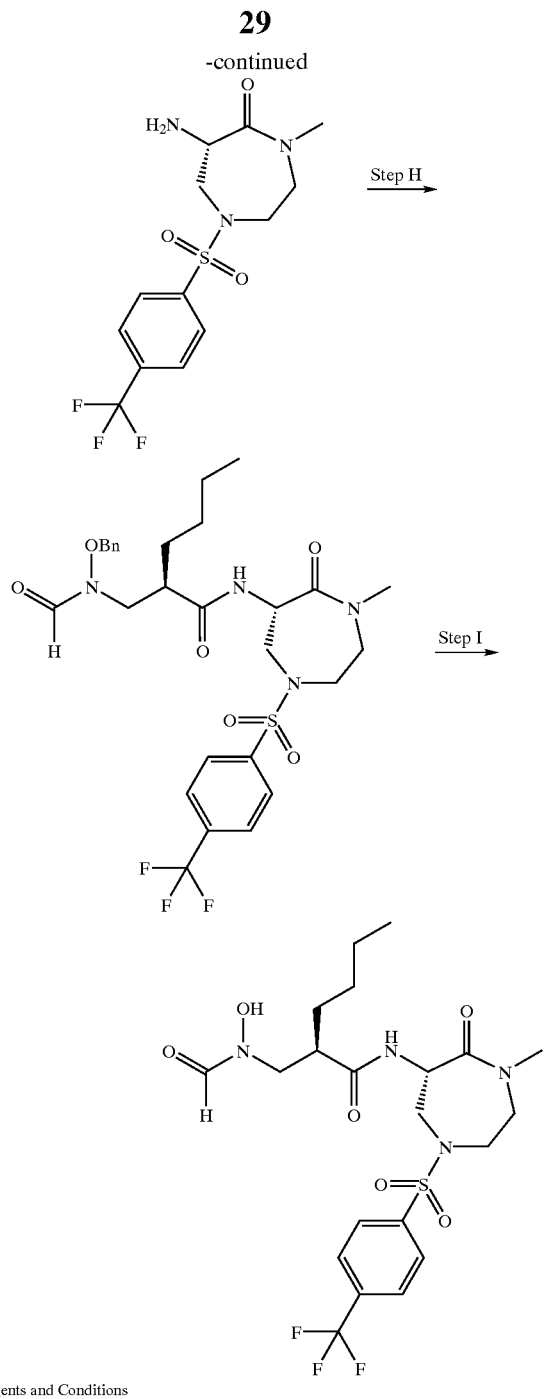

Reagents and Conditions
A: SOCl$_2$, MeOH, 4 h;
B: 2-[N-(tert-Butoxycarbonyl)-N-methylamino)] acetaldehyde, NaBH$_3$CN, MeOH/AcOH (99/1), 12 h;
C: HCl/Et$_2$O, 12 h;
D: LIOH, MeOH/H$_2$O (3/1), 3 h;
E: EDC, HOAt, DMF, 12 h;
F: Trifluoromethyl benzene sulfonyl chloride, Et$_3$N, DCM, 5 h;
G: HBr (45%), AcOH, 3 h;
H: 2R-[(Benzyloxy-formyl-amino)-methyl]-hexyl pentafluorophenyl ester, DMF, 12 h;
I: Pd/C, H$_2$, EtOH, 12 h.

Step A: 3-Amino-2S-benzyloxycarbonylamino-propionic Acid Methyl Ester, Hydrochloride To a cooled solution (0° C.) of 3-amino-2S-benzyloxycarbonylamino-propionic acid (1 g, 4.2 mmol) in methanol (15 ml) was added dropwise thionyl chloride (0.36 ml, 5.04 mmol). The reaction mixture was stirred for 4 hours at room temperature and concentrated in vacuo to give a white crystal (1.2 g, 99%). $^1$H-NMR; δ ((CD$_3$)$_2$SO): 8.25 (3H, br s), 7.92 (1H, d, J=8.3 Hz), 7.37 (5H, s), 5.07 (2H, s), 4.484.39 (1H, m), 3.68(3H, s) and 3.24–3.06 (2H,br s). LRMS: +ve ion 253 [M+H].

Step B: 2S-Benzytoxycarbonylamino-3-[2-(tert-butoxycarbonyl-methyl-amino)-ethylamino]-propionic Acid Methyl Ester, Hydrochloride 2-[N-(tert-Butoxycarbonyl)-N-methylamino)] acetaldehyde (S. Kato, H. Harada and T. Morie, *J. Chem. Soc., Perkin Trans.* 1, 1997, 3219 ) was added to a solution of 3-Amino-2S-benzyloxycarbonylamino-propionic acid methyl ester, hydrochloride in methanol/acetic acid (99/1, 12 ml). Over a period of 45 minutes, sodium cyano borohydride was added portionwise and the reaction mixture was stirred overnight at room temperature. The latter was diluted with ethyl acetate (150 ml) and a saturated solution of sodium bicarbonate was added at 0° C. The organic layer was washed with water (40 ml), brine (40 ml), dried over anhydrous magnesium sulphate and concentrated in vacuo. The crude reaction mixture was purified through flash chromatography (ethyl acetate) to give a clear oil (0.44 g, 63%). $^1$H-NMR; δ (CDCl$_3$) 7.35 (5H, s), 5.88–5.71 (1H,br s), 5.11 (2H, s), 4.41 (1H, m), 3.75 (3H, s), 3.26 (2H, m), 3.06–2.92 (2H, m), 2.83 (3H, s), 2.75 (2H, m). LRMS: +ve ion 410 [M+H]

Step C: 2S-Benzyloxycarbonylamino-3-(2-methylamino-ethylamino)-propionic Acid Methyl Ester, Dihydrochloride.

2S-Benzyloxycarbonylamino-3-[2-(tert-butoxycarbonyi-methyl-amino)ethylamino]-proprianic acid methyl ester, hydrochloride (200 mg, 0.49 mmol) was dissolved in diethyl ether (3 ml) under a blanket of argon. To the reaction mixture cooled in an ice bath, hydrogen chloride 1M in diethyl ether (1.5 ml, 1.5 mmol) was added. The reaction mixture was stirred overnight at room temperature and concentrated in vacuo to give the pure title compound (168 mg, 99%).$^1$H-NMR; δ (CDCl$_3$) 7.37 (5H, m), 5.14 (2H, s), 4.88 (1H, m), 3.77 (3H, s), 3.61–3.41 (6H, m), 2.77 (3H, s). LRMS: +ve ion 310 [M+H]

Step D: 2S-Benzyloxycarbonylamino-3-(2-methylamino-ethylaminoypropionic Acid, Dihydrochloride.

2S-Benzyloxycarbonylamino-3-(2-methylamino-ethylaminopropionic acid methyl ester, dihydrochloride (168 mg, 0.48 mmol) was dissolved in methanol/ water (3/1, 4 ml) and lithium hydroxide (101 mg, 2.4 mmol) was added to the reaction mixture at 5° C. The reaction mixture was stirred at room temperature for 4 h, and then concentrated in vacuo. The residue was dissolved in water (8 ml), acidified to pH =1 by means of 1M HCl and the solvent was removed in vacuo to give the pure title compound (0.15 g, 85%). $^1$H-NMR; δ (CD$_3$OD) 7.38 (5H, m), 5.14 (2H, s), 4.58 (1H, m), 3.65–3.45 (6H, m) and 2.77 (3H, s). LRMS: +ve ion 296 [M+H]

Step E: (1-Methyl-7-oxo-[1,4]diazepan-6S-yl)-carbamic Acid Benzyl Ester

2S-Benzyloxycarbonylamino-3-(2-methylamino-ethylamino)propionic acid, dihydrochloride (0.15 g, 0.4 mmol) was diluted in DMF (12 ml) and cooled in an ice bath. HOAt (8 mg, 0.06 mmol) and EDC (102 mg, 0.53 mmol) were added to the stirred solution and the stirring continued for 14 h. The reaction mixture was concentrated in vacuo. Purification through flash chromatography (dichloromethane-methanol: 9515) gave the pure title compound (60 mg, 54%). $^1$H-NMR; δ (CDCl$_3$) 7.35 (5H, s), 6.25 (1H, m), 5.11 (2H, s), 4.48 (1H, m), 3.76–3.66 (2H, m), 3.27–3.05 (5H, m), 2.97–2.66 (2H, m), 1.9 (2H, br s). LRMS: +ve ion 278 [M+H].

Step F: [4-Methyl-5-oxo-1-(4-trifluoromethyl-benzenesulfonyl)-[1,4]diazepan-6S-yl]-Carbamic Acid Benzyl Ester (1-Methyl-7-oxo-[1,4]diazepan-6S-yl)-carbamic acid benzyl ester (0.12 g, 0.43 mmol) was diluted in dry dichloromethane (5 ml) and cooled in an ice bath. Triethylamine (60 μl, 0.43 mmol) and 4-trifluoromethyl-benzenesulfonyl chloride (105 mg, 0.43 mmol) were added to the stirred solution and the stirring continued for 5 h. The reaction mixture was washed with water (5 ml), dried over anhydrous magnesium sulphate and concentrated under reduced pressure to give a white solid. (200 mg, 95%) $^1$H-NMR; δ (CDCl$_3$) 8.02 (2H, d, J=8.0 Hz), 7.80 (2H, d, J=8.0 Hz), 7.37 (5H, s), 6.22 (1H, m), 5.17 (2H, m), 4.53 (1H, m), 4.25 (1H, m), 4.03 (1H, m), 3.63 (1H, m), 3.32 (1H,m), 3.01 (3H, s), 2.82–2.60 (2H, m).

Step G: 6S-Amino-4-methyl-1-(4-trifluoromethyl-benzenesulfonyl)-[1,4]diazepan-5-one Hydrobromide To a cooled solution (0° C.) of [4-Methyl-5-oxo-1-(4-trifluoromethyl-benzenesulfonyl)-[1,4]diazepan-6S-yl]-carbamic acid benzyl ester (160 mg, 0.33 mmol) in acetic acid (2 ml), was added hydrogen bromide (45% in acetic acid, 2 ml). The reaction mixture was stirred for 3 hours at room temperature and 5 ml of diethyl ether was added to give a crystallisation. The white crystal was filtered off (0.14 g, 99%). $^1$H-NMR: δ (CD$_3$OD) 8.01 (4H, m), 4.48 (1H, m) 4.08–3.78 (3H, m), 3.57 (1H, m), 3.10–2.92 (5H, m). LMRS: +ve ion 352 [M+H]

Step H: 2R-[(Benzyloxy-formyl-amino)-methyl]-hexanoic acid [4-methyl-5-oxo-1-(4-trifluoromethyl-benzene-sulfonyl)-[1,4]diazepan-6S-yl]-amide To a solution of 2R-[(benzyloxy-formyl-amino)-methyl]-hexyl pentafluorophenyl ester (107 mg, 0.24 mmol) in DMF (6 ml) were added 6S-Amino-4-methyl-1-(4-trifluoromethyl-benzenesulfonyl)-[1,4] diazepan-5-one, hydrobromide (125 mg, 0.29 mmol) and triethylamine (66 μl, 0.48 mmol). The reaction mixture was stirred at room temperature for 14 h. The solvent was removed under reduced pressure and the residue was dissolved in dichloromethane. The triethylamine hydrobromide was filtered off, and the organic layer was concentrated in vacuo. The residue was taken-up in methanol (10ml). The excess of pentafluorophenol and amine were removed using scavenger resins, A-26 carbonate resin (3.5 mmol loading, 0.2 g, 0.72 mmol) and methylisocyanate polystyrene resin (1.2 mmol loading, 1.0 g, 1.2 mmol) respectively. A purification through flash chromatography (dichlormethane-methanol 99:1) gave the pure title compound (100 mg, 68%). $^1$H-NMR; δ (CDCl$_3$, rotamers) 8.07 (3H, m), 7.81 (2H, m), 7.38 (5H, br s), 7.01 (1H, br s), 5.014.68 (2H, m), 4.18 (1H, m), 3.89–3.48 (4H, m), 3.28 (1H, m), 3.01–2.88 (5H, m), 2.64–2.17 (2H, m), 1.74–1.25 (6H, m), 0.85 (3H, t, J=6.8 Hz). LRMS: +ve ion 635 [M+Na]

Step I: 2R-[(Formyl-hydroxy-aminoymethyl]-hexanoic acid [4-methyl-5-oxo-1-(4-trifluoromethyl-benzenesulfonyl)-[1,4]diazepan-6S-yl]-amide 2R-[(Benzyloxy-formyl-amino)-methyl]-hexanoic acid [4-methyl-5-oxo-1-(4-trifluoromethyl-benzenesulfonyl)-[1,4]diazepan-6S-yl]-amide (100 mg, 0.16 mmol) was dissolved in ethanol (10 ml) and placed under a blanket of argon. Palladium on charcoal (10 mg, 10% weight) was added and the reaction mixture was stirred vigorously while bubbling hydrogen gas for 45 minutes. The reaction mixture was then stirred for 12 hours under an atmosphere of hydrogen. The flask was purged with argon before removing the catalyst by filtration. The filtrate was concentrated under reduced pressure to provide the title compound as a colourless oil (75 mg, 88%). $^1$H-NMR; δ (CDCl$_3$, rotamers), 8.39 (0.25H, s), 8.04 (2H, d, J=8.2 Hz), 7.91 (0.75H, s), 7.82 (2H, d, J=8.1 Hz) 4.73 (1H, m), 3.87 (2H, m), 3.51 (1H, m), 3.32 (1H, m), 3.02 (3H, m), 2.87 (1H, m) 2.75 (1H,m), 1.84–1.23 (6H, m), 0.87 (3H, t, J=6.8 Hz). $^{13}$C-NMR; δ CDlC$_3$, rotamers), 172.9, 170.7, 141.0, 128.5, 128.3, 127.0, 126.9, 52.9, 52.5, 50.2, 48.9, 47.3, 45.2, 36.9, 29.8, 29.7, 23.0 and 14.2. LRMS: +ve ion 545 [M+Na].

What is claimed is:

1. A compound selected from the group consisting of:
   2R-[(Formyl-hydroxy-amino)-methyl]-hexanoic acid (4,7,7-trimethyl-5-oxo-[1,4]thiazepan-6R-yl) amide;
   2-[(Formyl-hydroxy-amino)-methyl]-hexanoic acid (5,5-dimethyl-7-oxo-[1,4]oxathiepan-6-yl)-amide;
   2-[(Formyl-hydroxy-amino)-methyl]-hexanoic acid (7,7-dimethyl-5-oxo-octahydro-8-thia-4a-aza-benzocyclohepten-6-yl)-amide;
   2-[(Formyl-hydroxy-amino)-methyl]-hexanoic acid (4-ethyl-7,7-dimethyl-5-oxo-[1,4]thiazapan-6-yl)-amide;
   2-[(Formyl-hydroxy-amino)-methyl]-hexanoic acid (4-propyl-7,7-dimethyl-5-oxo-[1,4]thiazapan-6-yl)-amide;
   2R-[(formyl-hydroxy-amino)-methyl]-hexanoic acid (1-benzyl-2-oxo-piperidin-3S-yl) amide;
   2R-[(Formyl-hydroxy-amino)-methyl]-hexanoic acid (2-oxo-azepan-3S-yl)-amide;
   2R-[(formyl-hydroxy-amino)-methyl]-hexanoic acid (2,9-dioxo-1,8 diaza-cyclotetradec- 3S-yl)-amide;
   2R-[(formyl-hydroxy-amino)-methyl]-hexanoic acid (2-oxo-azacyclotridec-3R,S-yl)-amide; and
   2R-[(Formyl-hydroxy-amino)-methyl]-hexanoic acid [4-methyl-5-oxo-1-(4-trifluoromethyl-benzenesufonyl)-[1,4]diazepan6S-yl]-amide.

2. A method for the treatment of bacterial infections in humans and non-human mammals, which comprises administering to a subject suffering such infection an antibacterially effective dose of a compound of formula (I) or a pharmaceutically or veterinarily acceptable salt, hydrate, or solvate thereof:

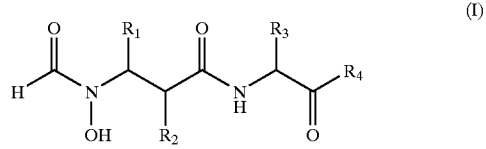

(I)

wherein:
   $R_1$ represents hydrogen, methyl, or trifluoromethyl;
   $R_2$ represents a group $R_{10}$-(X)$_n$-(ALK)- wherein
      $R_{10}$ represents hydrogen, a $C_1$–$C_6$ alkyl, $C_2$–$C_6$ alkenyl, $C_2$–$C_6$ alkynyl, cycloalkyl, aryl, or heterocyclyl group, any of which may be unsubstituted or substituted by ($C_1$–$C_6$)alkyl, ($C_1$–$C_6$)alkoxy, hydroxy, mercapto, ($C_1$–$C_6$)alkylthio, amino, halo, trifluoromethyl, cyano, nitro, -COOH, -CONH$_2$, -COOR$^A$, -NHCOR$^A$, -CONHR$^A$, -NHR$^A$, -NR$^A$R$^B$, or -CONR$^A$R$^B$ wherein R$^A$ and R$^B$ are independently a ($C_1$–$C_6$)alkyl group, and
      ALK represents a straight or branched divalent $C_1$–$C_6$ alkylene, $C_2$–$C_6$ alkenylene, $C_2$–$C_6$ alkynylene radical, and may be interrupted by one or more non-adjacent —NH—, —O— or —S— linkages,
   X represents —NH—, —O— or —S—, and n is 0 or 1; and R₃ and R₄, taken together with the carbon atoms to which they are respectively attached, form an optionally substituted saturated carbocyclic or heterocyclic ring of 5 to 16 atoms, which may be benz-fused or fused to a second optionally substituted saturated carbocyclic or heterocyclic ring of 5 to 16 atoms.

3. A method as claimed in claim 2 wherein R₁ is hydrogen.

4. A method as claimed in claim 3 wherein R₂ is

C₁–C₆ alkyl, C₃–C₆ alkenyl or C₃–C₆ alkynyl;

phenyl(C₁–C₆ alkyl)-, phenyl(C₃–C₆ alkenyl)- or phenyl (C₃–C₆ alkynyl)- optionally substituted in the phenyl ring;

cycloalkyl(C₁–C₆ alkyl)-, cycloalkyl(C₃–C₆ alkenyl)- or cycloalkyl (C₃–C₆ alkynyl)- optionally substituted in the phenyl ring;

heterocyclyl(C₁–C₆ alkyl)-, heterocyclyl(C₃–C₆ alkenyl)- or heterocyclyl (C₃–C₆ alkynyl)- optionally substituted in the heterocyclyl ring; or 4-phenylphenyl(C₁–C₆ alkyl)-, 4-phenylphenyl(C₃–C₆ alkenyl)-, 4-phenylphenyl(C₃–C₆ alkynyl)-, 4-heteroarylphenyl(C₁–C₆ alkyl)-, 4-heteroarylphenyl (C₃–C₆ alkenyl)-, 4-heteroarylphenyl(C₃–C₆ alkynyl)-, optionally substituted in the terminal phenyl or heteroaryl ring.

5. A method as claimed in claim 3 wherein R₂ is methyl, ethyl, n- and iso-propyl, n- and iso-butyl, n-pentyl, isopentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, or 4-methoxybenzyl.

6. A method as claimed in claim 3 wherein R₂ is n-propyl, n-butyl, n-pentyl, benzyl or cyclopentylmethyl.

7. A method as claimed in claim 3 wherein the ring formed by R₃ and R₄ taken together with the carbon atoms to which they are respectively attached has from 5 to 8 ring atoms.

8. A method as claimed in claim 3 wherein the ring formed by R₃ and R₄ taken together with the carbon atoms to which they are respectively attached, has structure (III):

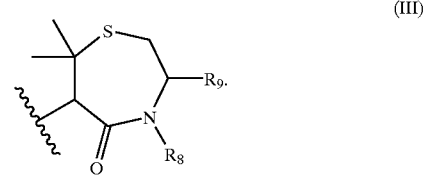

9. A method as claimed in claim 8 wherein R₈ is hydrogen, methyl, ethyl, n-propyl, cyclopentyl, phenyl or benzyl, and R₉ is hydrogen, isobutyl, phenyl or benzyl.

* * * * *

UNITED STATES PATENT AND TRADEMARK OFFICE
CERTIFICATE OF CORRECTION

PATENT NO. : 6,503,897 B1
DATED : January 7, 2003
INVENTOR(S) : Raymond Paul Beckett et al.

It is certified that error appears in the above-identified patent and that said Letters Patent is hereby corrected as shown below:

Column 32,
Line 34, "benzenesufonyl" has been replaced with -- benzenesulfonyl --;
Line 35, "diazepan6S-yl" has been replaced with -- diazepam-6S-yl --;

Column 34,
Line 3, "but2-yn-1-yl" has been replaced with -- but-2-yn-1-yl --.

Signed and Sealed this

Sixth Day of May, 2003

JAMES E. ROGAN
*Director of the United States Patent and Trademark Office*